(12) United States Patent
Tsuda et al.

(10) Patent No.: US 6,172,102 B1
(45) Date of Patent: Jan. 9, 2001

(54) PYRROLE DERIVATIVES AND MEDICINAL COMPOSITION

(75) Inventors: Masami Tsuda, Kyoto; Mitsushi Tanaka, Shiga; Ayatsugu Nakamura, Nara, all of (JP)

(73) Assignee: Nippon Shinyaku Co., Ltd., Kyoto (JP)

( * ) Notice: Under 35 U.S.C. 154(b), the term of this patent shall be extended for 0 days.

(21) Appl. No.: 09/365,096

(22) Filed: Jul. 30, 1999

Related U.S. Application Data

(62) Division of application No. 08/973,369, filed on Dec. 8, 1997, now Pat. No. 5,998,459.

(30) Foreign Application Priority Data

Jun. 7, 1995 (JP) .................................................. 7-140698
Jun. 6, 1996 (WO) ................................... PCT/JP96/01526

(51) Int. Cl.[7] ..................... C07D 403/04; A61K 31/4025
(52) U.S. Cl. ........................................... 514/422; 548/518
(58) Field of Search .............................. 514/422; 548/518

(56) References Cited

U.S. PATENT DOCUMENTS

| | | | | |
|---|---|---|---|---|
| 4,431,823 | * | 2/1984 | Fryer et al. ........................... | 548/561 |
| 4,737,513 | * | 4/1988 | Tessier et al. ........................ | 514/427 |
| 4,966,901 | * | 10/1990 | Zollet et al. ......................... | 514/211 |
| 5,359,090 | * | 10/1994 | Doehner et al. ...................... | 548/561 |
| 5,998,459 | * | 12/1999 | Tsuda et al. .......................... | 514/408 |

* cited by examiner

*Primary Examiner*—Joseph K. McKane
*Assistant Examiner*—Sonya Wright

(57) ABSTRACT

The invention relates to a pharmaceutical composition comprising a pyrrole derivative of the following formula [1] or a pharmaceutically acceptable salt thereof, or a solvate of either of them, as an active ingredient.

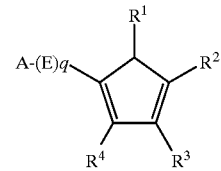

[1]

(wherein $R^1$ represents hydrogen or alkoxycarbonylamino, $R^2$ represents alkyl, aryl which may be substituted, aromatic heterocyclyl which may be substituted, unsubstituted amino, monoalkylamino, dialkylamino, or cyclic amino which may be substituted; $R^3$ represents cyano or carbamoyl; $R^4$ represents hydrogen or alkyl; E represents alkylene; q is equal to 0 or 1, A represents methyl, aryl which may be substituted, or aromatic heterocyclyl which may be substituted)

The pharmaceutical composition of the invention is effective for the treatment of pollakiuria or urinary incontinence.

8 Claims, No Drawings

PYRROLE DERIVATIVES AND MEDICINAL COMPOSITION

This application is a Division of Ser. No. 08/973,369 filed Dec. 8, 1997, now U.S. Pat. No. 5,998,459.

TECHNICAL FIELD

The present invention relates to a pyrrole derivative, a pharmaceutically acceptable salt thereof, and a solvate of either of them, all of which are useful as medicines.

The compound of the invention has urinary bladder capacity increasing activity and is useful for the treatment of pollakiuria and urinary incontinence.

BACKGROUND ART

The frequency of urination of healthy humans is generally 4–6 times a day and usually no urine is voided during sleep at night. The condition of an abnormally increased frequency of urination is called pollakiuria and the condition of involuntary emptying of the urinary bladder is known as urinary incontinence. Both morbidities are bothersome to the affected person because sleep is disturbed and going out is restricted. The frequency of occuring pollakiuria or urinary incontinence is particularly high in the bedridden aged persons and patients with dementia and there is a pressing need for development of useful therapeutic drug in this field, not only for patients and clinical doctors but also for the people taking charge of nursing care.

As therapeutic drugs designed to ameliorate pollakiuria and urinary incontinence through increase in bladder capacity, flavoxate, oxybutynin, propiverine and so on are used today.

Meanwhile, as pyrrole derivatives apparently resembling the compound of the present invention, the compounds listed below in Table 1 are known. However, none of them are known to have the first medicinal use, namely, to be useful for the treatment of disease such as pollakiuria or urinary incontinence.

TABLE 1

| Compound No. | Structural formula | Literature |
|---|---|---|
| R1 | | J. Prakt. Chem., 318, 663 (1976). |
| R2 | | J. Heterocyclic Chem., 14, 383 (1977). Z. Chem., 1, 349 (1961). |
| R3 | | J. Heterocyclic Chem., 14, 383 (1977). |
| R4 | | J. Heterocyclic Chem., 14, 383 (1977). |
| R5 | | Khim. Geterotsiki. Soedim., (9), 1217, (1975) (Chem. Abstr., 84,59299 (1976)) |

TABLE 1-continued

| Compound No. | Structural formula | Literature |
|---|---|---|
| R6 | | J. Heterocyclic Chem., 14, 383 (1977). |
| R7 | | Khim. Geterotsiki. Soedim., (9), 1217, (1975) (Chem. Abstr., 84,59299 (1976)) |
| R8 | | J. Pharm. Sci., 68, 317 (1979). |
| R9 | | Synthesis, 217 (1979). |
| R10 | | Synthesis, 55 (1974). |
| R11 | | J. Pharm. Sci., 65, 908 (1976). J. Heterocyclic Chem., 23, 397 (1986). |
| R12 | | Farmaco, Ed. Sc., 43, 103 (1988). |

TABLE 1-continued

| Compound No. | Structural formula | Literature |
|---|---|---|
| R13 | | Khim. Geterotsiki. Soedim., (9), 1217, (1975) (Chem. Abstr., 84, 59299 (1976)) |
| R14 | | J. Heterocyclic Chem., 14, 383 (1977). |
| R15 | | Khim. Geterotsiki. Soedim., (9), 1217, (1975) (Chem. Abstr., 84, 59299 (1976)) |
| R16 | | Farmaco, Ed. Sc., 43, 103 (1988). |
| R17 | | Farmaco, Ed. Sc., 43, 103 (1988). |
| R18 | | Farmaco, Ed. Sc., 43, 103 (1988). |

TABLE 1-continued

| Compound No. | Structural formula | Literature |
|---|---|---|
| R19 | (4-nitrophenyl)-pyrrole-CN-pyrrolidine | Farmaco, Ed. Sc., 43, 103 (1988). |
| R20 | (2,4-dimethylphenyl)-pyrrole-CN-pyrrolidine | Farmaco, Ed. Sc., 43, 103 (1988). |
| R21 | phenyl-pyrrole-CN-piperidine | Farmaco, Ed. Sc., 43, 103 (1988). |
| R22 | (4-bromophenyl)-pyrrole-CN-piperidine | Farmaco, Ed. Sc., 43, 103 (1988). |
| R23 | phenyl-pyrrole-CN-morpholine | Farmaco, Ed. Sc., 43, 103 (1988). |
| R24 | phenyl-pyrrole-CN-N(Et)$_2$ | Farmaco, Ed. Sc., 43, 103 (1988). |

TABLE 1-continued

| Compound No. | Structural formula | Literature |
|---|---|---|
| R25 | | Farmaco, Ed. Sc., 43, 103 (1988). |
| R26 | | Farmaco, Ed. Sc., 43, 103 (1988). |
| R27 | | Farmaco, Ed. Sc., 43, 103 (1988). |
| R28 | | Farmaco, Ed. Sc., 43, 103 (1988). |
| R29 | | J. Chem. Res., Synop. (8), 266 (1992). J. Chem. Res., Miniprint, 2049 (1992). |
| R30 | | Heterocycles, 10, 261 (1978). |

TABLE 1-continued

| Compound No. | Structural formula | Literature |
| --- | --- | --- |
| R31 | | Heterocycles, 10, 261 (1978). |
| R32 | | J. Org. Chem., 43, 4273 (1978).<br>J. Chem. Soc., B, (1), 79 (1970). |
| R33 | | J. Org. Chem., 43, 4273 (1978). |
| R34 | | J. Org. Chem., 43, 4273 (1978).<br>EP 358047 A2. |
| R35 | | J. Org. Chem., 43, 4273 (1978). |
| R36 | | J. Org. Chem., 43, 4273 (1978). |
| R37 | | J. Org. Chem., 43, 4273 (1978).<br>Heterocycles, 20, 829 (1983). |

TABLE 1-continued
| Compound No. | Structural formula | Literature |
| --- | --- | --- |
| R38 | 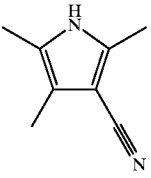 | J. Chem. Soc., B, (1), 79 (1970). |
| R39 | 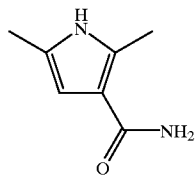 | Gazz. Chim. Ital., 71, 375 (1941). |
| R40 | 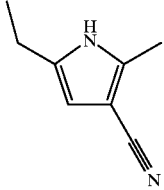 | Justus Liebigs Ann. Chem., 447, 43 (1926). |
| R41 | 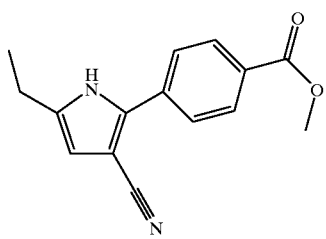 | WO 93/19067. |
| R42 | 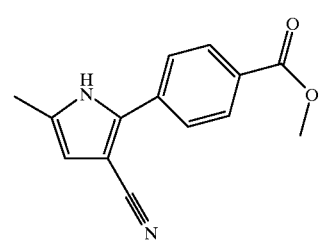 | EP 480204 A1. |
| R43 | 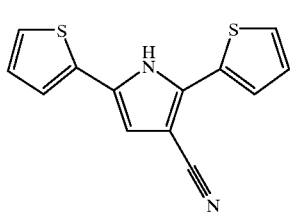 | EP 314009 A2.<br>EP 389904 A2. |

TABLE 1-continued

| Compound No. | Structural formula | Literature |
|---|---|---|
| R44 | (2-phenyl-5-(4-nitrophenyl)-1H-pyrrole-3-carbonitrile) | Chem. Ber., 105, 1258 (1972). |
| R45 | (5-phenyl-2-(isoquinolin-1-yl)-1H-pyrrole-3-carboxamide) | J. Org. Chem., 31, 4110 (1996). |
| R46 | (5-phenyl-2-(isoquinolin-1-yl)-1H-pyrrole-3-carbonitrile) | J. Org. Chem., 31, 4110 (1996). |
| R47 | (5-(thiophen-2-yl)-2-(furan-2-yl)-1H-pyrrole-3-carbonitrile) | EP 389904 A2. |
| R48 | (2,5-di(furan-2-yl)-1H-pyrrole-3-carbonitrile) | EP 389904 A2. |
| R49 | (2-(furan-2-yl)-5-(thiophen-2-yl)-1H-pyrrole-3-carbonitrile) | EP 389904 A2. |

DISCLOSURE OF INVENTION

The inventors of the present invention did much research for developing a drug which is structurally different from the hitherto-known therapeutic drugs for pollakiuria or urinary incontinence and is more useful than those drugs.

As a result, the inventors found that the pyrrole derivative of the following formula [1] or a pharmaceutically acceptable salt thereof, or a solvate of either of them, has excellent bladder capacity increasing activity and is useful as a therapeutic drug for pollakiuria or urinary incontinence. The present invention has been completed on the basis of the above finding.

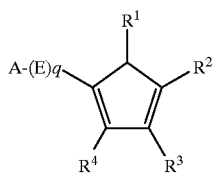

[1]

wherein $R^1$ represents hydrogen or alkoxycarbonylamino;
$R^2$ represents (1) alkyl, (2) aryl which may be substituted, (3) aromatic heterocyclyl which may be substituted,

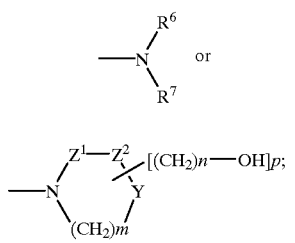

(4) or (5)

$R^6$ and $R^7$ may be the same or different and each represents (1) hydrogen or (2) alkyl (which alkyl may be substituted by (1) hydroxy, (2) aryl which may be substituted by alkoxy, or (3) aromatic heterocyclyl);
$Z^1$ and $Z^2$ may be the same or different and each represents $-CH_2-$ or $>C=O$; provided that $Z^1$ and $Z^2$ do not concurrently represent $>C=O$;
Y represents $-CH_2-$, $-O-$, $-S-$, or $>NR^9$;
$R^9$ represents hydrogen, alkyl, acyl, aryl, or aromatic heterocyclyl;
m represents an integer of 1–3; n represents an integer of 0–2; p represents 0 or 1;
in case $R^2$ represents aryl which may be substituted or aromatic heterocyclyl which may be substituted, the aryl or aromatic heterocyclyl may be substituted by 1 member or 2–3 different members selected from the group consisting of (1) halogen, (2) alkyl which may be substituted by halogen, (3) cyano, (4) nitro, (5) alkoxycarbonyl, (6) hydroxy, (7) alkoxy (which alkoxy may be substituted by halogen, aryl which may be substituted by alkoxy, or alkoxy), (8) $-NHSO_2R^{82}$, and (9) $-NR^{83}R^{84}$; or two adjacent substituent groups may jointly represent $-O-(CH_2)_t-O-$;
$R^{82}$ represents (1) alkyl or (2) aryl which may be substituted by alkyl;
t represents 1 or 2;
$R^{83}$ or $R^{84}$ may be the same or different and each represents (1) hydrogen, (2) alkyl, or (3) acyl; or $R^{83}$ and $R^{84}$ jointly and taken together with the adjacent N atom are present 5- through 7-membered cyclic amino;
$R^3$ represents cyano or carbamoyl;
$R^4$ represents hydrogen or alkyl;
E represents alkylene; q represents 0 or 1;
A represents (1) methyl, (2) aryl which may be substituted, or (3) aromatic heterocyclyl which may be substituted;
in case A represents aryl which may be substituted or aromatic heterocyclyl which may be substituted, the aryl or aromatic heterocyclyl may be substituted by 1 member or 2–3 different members selected from the group consisting of (1) halogen, (2) alkyl which may be substituted by halogen, (3) cyano, (4) nitro, (5) alkoxycarbonyl, (6) hydroxy, (7) alkoxy (which alkoxy may be substituted by a halogen, aryl which may be substituted by alkoxy, or alkoxy), (8) $-NHSO_2R^{92}$, and (9) $-NR^{93}R^{94}$; or two adjacent substituent groups may jointly represent $-O-(CH_2)_u-O-$;
$R^{92}$ represents (1) alkyl or (2) aryl which may be substituted by alkyl;
u represents 1 or 2;
$R^{93}$ and $R^{94}$ may be the same or different and each represents (1) hydrogen, (2) alkyl, or (3) acyl; or $R^{93}$ and $R^{94}$ jointly and taken together with the adjacent N atom represent 5- through 7-membered cyclic amino;
$A-(E)_q$, $R^4$, and the double bond of the pyrrole ring may jointly, i.e.

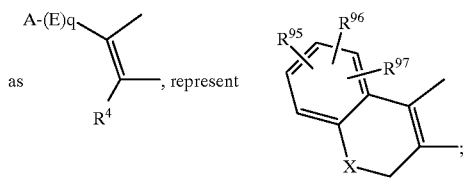

as , represent ;

X represents $-O-$, $-S-$, or $>NR^{90}$ where $R^{90}$ represents alkyl;
$R^{95}$, $R^{96}$ and $R^{97}$ may be the same or different and each is selected from the group consisting of (1) hydrogen, (2) halogen, (3) alkyl which may be substituted by halogen, (4) cyano, (5) nitro, (6) alkoxycarbonyl, (7) hydroxy, (8) alkoxy (which alkoxy may be substituted by halogen or alkoxy), (9) $-NHSO_2R^{92}$ ($R^{92}$ is as defined above), and (10) $-NR^{93}R^{94}$ ($R^{93}$ and $R^{94}$ are as defined above); any two adjacent substituent groups among $R^{95}$, $R^{96}$, and $R^{97}$ may jointly represent $-O-(CH_2)_u-O-$ (u is as defined above).

The present invention relates to a pharmaceutical composition comprising the compound of formula [1] as an active ingredient. The present invention further relates to the compound of formula [1].

Depending on the combination of specific substituent groups, the compound of formula [1] includes known compounds. However, it was discovered for the first time by the inventors of the present invention that those known compounds have bladder capacity increasing activity.

Thus, among pyrrole derivatives of formula [1], the following compound (1)–(28) are known compounds, while the other compounds are novel compounds not described in any literature.

(1) the compound in which $R^1$ is hydrogen, $R^2$ is $NH_2$, $R^3$ is cyano, $R^4$ is methyl, q is equal to 0, and A is methyl, phenyl, or 4-hydroxyphenyl, (2) the compound in which $R^1$ is hydrogen, $R^2$ is $NH_2$, $R^3$ is cyano, $R^4$ is methyl, $-(E)q-$ is $-CH_2-$, and A is methyl, phenyl, 4-hydroxyphenyl, 4-chlorophenyl, or 3-indolyl, (3) the compound in which $R^1$ is hydrogen, $R^2$ is morpholino, $R^3$ is cyano, $R^4$ is hydrogen, q is equal to 0, and A is methyl or phenyl, (4) the compound in which $R^1$ is hydrogen, $R^2$ is 1-pyrrolidinyl, $R^3$ is cyano, $R^4$ is hydrogen, q is equal to 0, and A is phenyl, 4-bromophenyl, 4-nitrophenyl, or 2,4-dimethylphenyl, (5) the compound in which $R^1$ is hydrogen, $R^2$ is 1-piperidinyl, $R^3$ is cyano, $R^4$ is hydrogen, q is equal to 0, and A is phenyl or 4-bromophenyl, (6) the compound in which $R^1$ is hydrogen, $R^2$ is diethylamino, $R^3$ is cyano, $R^4$ is hydrogen, q is equal to 0, and A is methyl, phenyl, 4-bromophenyl, 3-nitrophenyl, (7) the compound in which $R^1$ is hydrogen, $R^2$ is $NH_2$, $R^3$ is cyano, $R^4$ is methyl, —(E)q— is —$CH_2CH_2$—, and A is methyl, (8) the compound in which $R^1$ is hydrogen, $R^2$ is $NH_2$, $R^3$ is cyano, $R^4$ is n-propyl, —(E)q— is —$CH_2$—, and A is methyl, (9) the compound in which $R^1$ is hydrogen, $R^2$ is $NH_2$, $R^3$ is cyano, $R^4$ is methyl, —(E)q— is —$CH(CH_3)CH_2$—, and A is methyl,

(10) the compound in which $R^1$ is hydrogen, $R^2$ is $NH_2$, $R^3$ is cyano, $R^4$ is ethyl, q is equal to 0, and A is methyl, (1) the compound in which $R^1$ is hydrogen, $R^2$ is methylamino, $R^3$ is cyano, $R^4$ is methyl, q is equal to 0, , and A is methyl, 12) the compound in which $R^1$ is hydrogen, $R^2$ is 2-oxopyrrolidin-1-yl, $R^3$ is cyano, $R^4$ is methyl, q is equal to 0, and A is methyl,

(13) the compound in which $R^1$ is hydrogen, $R^2$ is 1-piperidinyl, $R^3$ is cyano, $R^4$ is methyl, q is equal to 0, and A is phenyl,

(14) the compound in which $R^1$ is hydrogen, $R^2$ is n-butylamino, $R^3$ is cyano, $R^4$ is hydrogen, q is equal to 0, and A is phenyl,

(15) the compound in which $R^1$ is hydrogen, $R^2$ is methyl, $R^3$ is cyano, $R^4$ is methyl, q is equal to 0, and A is methyl or phenyl,

(16) the compound in which $R^1$ is hydrogen, $R^2$ is methyl, $R^3$ is carbamoyl, $R^4$ is methyl, q is equal to 0, and A is methyl,

(17) the compound in which $R^1$ is hydrogen, $R^2$ is methyl, $R^3$ is carbamoyl, $R^4$ is hydrogen, q is equal to 0, and A is methyl or phenyl,

(18) the compound in which $R^1$ is hydrogen, $R^2$ is methyl, $R^3$ is carbamoyl, $R^4$ is hydrogen, q is equal to 0, and A is methyl or phenyl,

(19) the compound in which $R^1$ is hydrogen, $R^2$ is methyl, $R^3$ is cyano, $R^4$ is hydrogen, —(E)q— is —$CH(CH_3)CH_2$—, and A is methyl,

(20) the compound in which $R^1$ is hydrogen, $R^2$ is phenyl, $R^3$ is cyano, $R^4$ is hydrogen, q is equal to 0, and A is methyl or phenyl,

(21) the compound in which $R^1$ is hydrogen, $R^2$ is isobutyl, $R^3$ is cyano, $R^4$ is hydrogen, q is equal to 0, and A is methyl,

(22) the compound in which $R^1$ is hydrogen, $R^2$ is 4-methoxycarbonylphenyl, $R^3$ is cyano, $R^4$ is hydrogen, q is equal to 0, and A is methyl,

(23) the compound in which $R^1$ is hydrogen, $R^2$ is 4-methoxycarbonylphenyl, $R^3$ is cyano, $R^4$ is hydrogen, —(E)q— is —$CH_2$—, and A is methyl,

(24) the compound in which $R^1$ is hydrogen, $R^2$ is 2-thienyl, $R^3$ is cyano, $R^4$ is hydrogen, q is equal to 0, and A is 2-thienyl or 2-furyl,

(25) the compound in which $R^1$ is hydrogen, $R^2$ is 4-nitrophenyl, $R^3$ is cyano, $R^4$ is hydrogen, q is equal to 0, and A is phenyl,

(26) the compound in which $R^1$ is hydrogen, $R^2$ is 1-isoquinolyl, $R^3$ is cyano or carbamoyl, $R^4$ is hydrogen, q is equal to 0, and A is phenyl,

(27) the compound in which $R^1$ is hydrogen, $R^2$ is 2-furyl, $R^3$ is cyano, $R^4$ is hydrogen, q is equal to 0, and A is 2-thienyl or 2-furyl,

(28) the compound in which $R^1$ is hydrogen, $R^2$ is methyl, $R^3$ is cyano, $R^4$ is methyl, —(E)q— is —$CH_2$—, and A is methyl.

The alkyl in formula [1] includes straight-chain or branched alkyl group of 1–4 carbon atoms, such as methyl, ethyl, n-propyl, isopropyl, n-butyl, isobutyl, sec-butyl, or tert-butyl.

The aryl includes aryl group of 6–12 carbon atoms, such as phenyl, 1-naphthyl, 2-naphthyl, 3-biphenyl, or 4-biphenyl.

The aromatic heterocyclyl includes aromatic 5- or 6-membered heterocyclyl group containing 1–4 heteroatoms selected from among nitrogen, oxygen and sulfur, and the corresponding benzologue (benzene-fused) systems (provided that 2-pyrrolyl and 3-pyrrolyl are excluded), such as 2-pyridyl, 3-pyridyl, 4-pyridyl, 2-pyrimidinyl, 4-pyrimidinyl, 1-indolyl, 2-indolyl, 3-indolyl, 1-tetrazolyl, 2-furyl, 3-furyl, 2-benzofuranyl, 3-benzofuranyl, 2-thienyl, and 3-thienyl.

The alkylene includes straight-chain or branched alkylene group of 1–4 carbon atoms, such as the following.

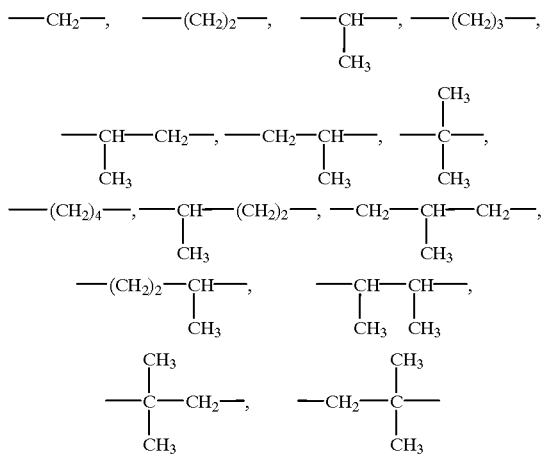

The alkyl moiety of said alkoxy, alkoxycarbonyl, or alkoxycarbonylamino includes the alkyl group mentioned above by way of example.

The halogen includes fluorine, chlorine, bromine, and iodine.

The acyl includes acyl group of 1–7 carbon atoms, such as formyl, acetyl, propionyl, butyryl, isobutyryl, valeryl, isovaleryl, pivaloyl, hexanoyl, isohexanoyl, or benzoyl.

The 5- through 7-membered cyclic amino represented by $NR^{83}R^{84}$ or $NR^{93}R^{94}$ includes 1-pyrrolidinyl, 1-piperidinyl, and 1-hexamethyleneimino, among others.

Preferred species of the compound [1] of the invention include those in which $R^2$ is

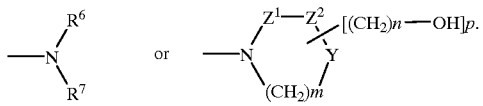

Still more preferred species of compound [1] according to the present invention are those in which $R^1$ is hydrogen, $R^2$ is $NH_2$, $R^3$ is cyano, $R^4$ is hydrogen or alkyl, q is equal to 0, and A is aryl which may be substituted or aromatic heterocyclyl which may be substituted.

Particularly preferred species of compound [1] according to the present invention are the following compounds (1)–(6).

(1) the compound in which $R^1$ is hydrogen, $R^2$ is $NH_2$, $R^3$ is cyano, $R^4$ is methyl, q is equal to 0, and A is phenyl, (2) the compound in which $R^1$ is hydrogen, $R^2$ is $NH_2$, $R^3$ is cyano, $R^4$ is methyl, q is equal to 0, and A is 2-fluorophenyl, (3) the compound in which $R^1$ is hydrogen, $R^2$ is $NH_2$, $R^3$ is cyano, $R^4$ is methyl, q is equal to 0, and A is 2,5-difluorophenyl, (4) the compound in which $R^1$ is hydrogen, $R^2$ is $NH_2$, $R^3$ is cyano, $R^4$ is methyl, q is equal to 0, and A is 3-pyridyl, (5) the compound in which $R^1$ is hydrogen, $R^2$ is $NH_2$, $R^3$ is cyano, $R^4$ is hydrogen, q is equal to 0, and A is phenyl, (6) the compound in which $R^1$ is hydrogen, $R^2$ is $NH_2$, $R^3$ is cyano, $R^4$ is hydrogen, q is equal to 0, and A is 4-fluorophenyl, The compound [1] according to the present invention can be produced, for example, by the following processes.

Synthetic Process A (production of compound [1a] corresponding to formula [1] wherein $R^1$ is hydrogen and $R^2$ is

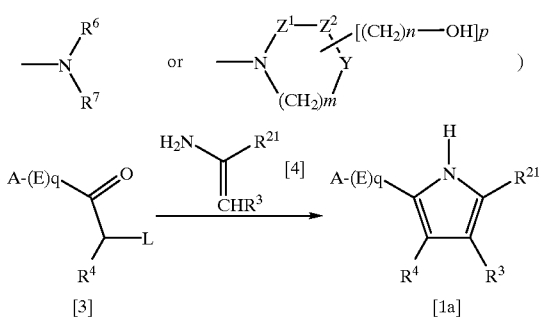

[In the above reaction schema, A, E, q, $R^3$, and $R^4$ are as defined hereinbefore; $R^{21}$ represents

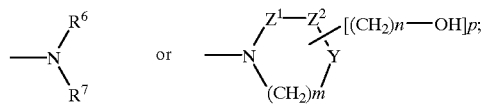

$R^6$, $R^7$, $Z^1$, $Z^2$, Y, m, n, and p are as defined hereinbefore; L represents halogen such as chlorine, bromine, or iodine]

Compound [1a] can be synthesized by reacting compound [3] with compound [4].

This reaction can be generally carried out in a solvent that does not interfere with the reaction (e.g. alcohols such as methanol, ethanol, n-propanol, isopropanol, n-butanol and tert-butanol, ethers such as tetrahydrofuran (THF) and diethyl ether, halogenated hydrocarbons such as chloroform and methylene chloride, hydrocarbons such as benzene, toluene and n-hexane, polar solvents such as acetonitrile, N,N-dimethylformamide (DMF), dimethyl sulfoxide (DMSO) and ethyl acetate and mixture of such solvents), either in the presence of a base (e.g.) ammonia, sodium hydrogen carbonate, potassium hydrogen carbonate, potassium carbonate, sodium carbonate, pyridine, 4-dimethylaminopyridine, triethylamine) or in the absence of the base, at −20 to 100° C. The reaction time is dependent on the species of compound [3] and compound [4] used and the reaction temperature but may generally range from 1 minute to 24 hours. The molar ratio of compound [4] to compound [3] is generally 1–2:1. Compound [4] may be used in excess so that it may function as the base as well.

Synthetic Process B (production of compound [1b] corresponding to formula [1] wherein $R^1$ is hydrogen and $R^2$ is $NH_2$)

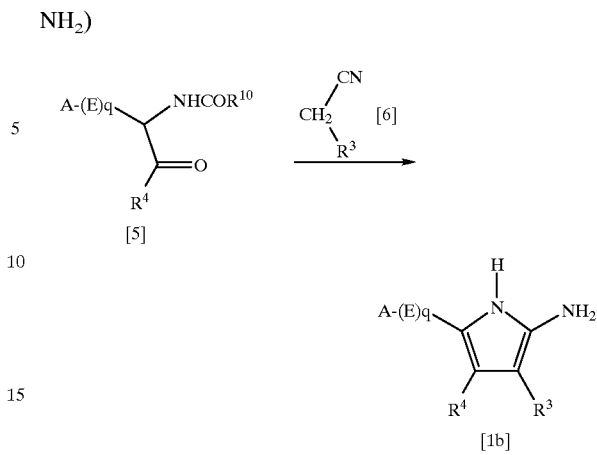

[In the above reaction schema, A, E, q, $R^3$, and $R^4$ are as defined above; $R^{10}$ represents alkyl such as that mentioned hereinbefore]

Compound [1b] can be synthesized by reacting compound [5] with compound [6].

This reaction can be generally carried out in a solvent that does not interfere with the reaction (e.g. alcohols such as methanol, ethanol, n-propanol, isopropanol, n-butanol and tert-butanol, ethers such as tetrahydrofuran (THF) and diethyl ether, halogenated hydrocarbons such as chloroform and methylene chloride, hydrocarbons such as benzene, toluene and n-hexane, polar solvents such as acetonitrile, N,N-dimethylformamide (DMF), dimethyl sulfoxide (DMSO), and mixture of such solvents), within the pH range of 9.5–10.5 as adjusted by addition of a base (e.g. a sodium alkoxide such as sodium methoxide or sodium ethoxide, piperidine, triethylamine, 30–60% aqueous solution of sodium hydroxide, 30–60% aqueous solution of potassium hydroxide) at −10 to 100° C. The reaction time is dependent on the species of compound [5] and compound [6] and the reaction temperature but may generally range from 5 minutes to 24 hours. The molar ratio of compound [6] to compound [5] is generally 1–2:1.

Synthetic Process C (production of compound [1c] corresponding to formula [1] wherein $R^1$ is alkoxycarbonyl amino and $R^2$ is

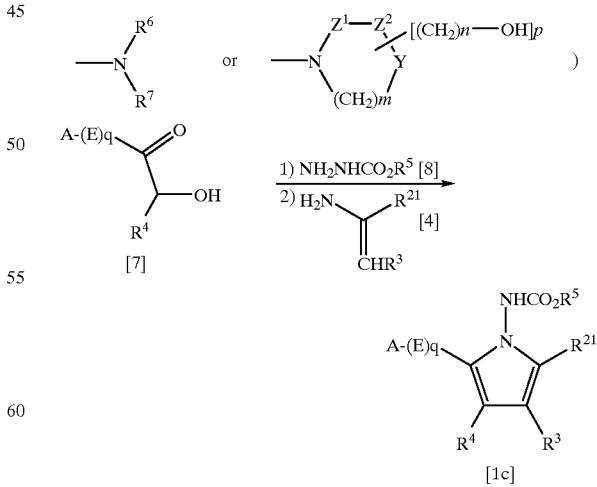

[In the above reaction schema, A, E, q, $R^{21}$, $R^3$, and $R^4$ are as defined hereinbefore; $R^5$ represents a straight-chain or branched alkyl group of 1–4 carbon atoms]

Compound [1c] can be synthesized by reacting compound [7] with compound [8] in the known manner (J. Heterocyclic Chem., 17, 1793, 1980) and subjecting the reaction product further to reaction with compound [4].

The reaction of compound [7] with compound [8] can be generally carried out in a solvent which does not interfere with the reaction (e.g. ethers such as tetrahydrofuran (THF) and diethyl ether, halogenated hydrocarbons such as chloroform and methylene chloride, hydrocarbons such as benzene, toluene and n-hexane, polar solvents such as acetonitrile, N,N-dimethylformamide (DMF), dimethyl sulfoxide (DMSO), and mixture of such solvents), either in the presence of a catalytic amount of an acid (e.g. concentrated hydrochloric acid, zinc chloride, boron trifluoride) or in the absence of the acid, at 0–150°C., while the byproduct water is continuously distilled off.

To this reaction mixture is added compound [4] at 10–30° C. and the whole mixture is heated at 40–100° C. The reaction time depends on the species of compound [7], compound [8], and compound [4] used and the reaction temperature but may generally range from 30 minutes to 24 hours. The proportions of compound [8] and compound [4] are generally 1–1.2 molar equivalents based on compound [7].

Synthetic Process D (production of compound [1d] corresponding to formula [1] wherein $R^1$ is alkoxycarbonylamino and $R^2$ is $NH_2$)

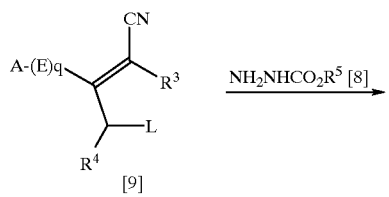

[In the above reaction schema, A, E, q, $R^3$, $R^4$, $R^5$, and L are as defined hereinbefore]

Compound [1d] can be synthesized by reacting compound [9] with compound [8] in the known manner (J. Prakt. Chem., 318, 663, 1976).

This reaction can be generally carried out in a solvent which does not interfere with the reaction (e.g. alcohols such as methanol, ethanol, n-propanol, isopropanol, n-butanol and tert-butanol, ethers such as tetrahydrofuran (THF) and diethyl ether, halogenated hydrocarbons such as chloroform and methylene chloride, hydrocarbons such as benzene, toluene and n-hexane, polar solvents such as acetonitrile, N,N-dimethyl-formamide (DMF) and dimethyl sulfoxide (DMSO), and mixture of such solvents) at 20–100° C. The reaction time is dependent on the species of compound [9] and compound [8] and the reaction temperature but may generally range from 30 minutes to 24 hours. The molar ratio of compound [8] to compound [9] is generally 1–1.2:1.

Synthetic Process E (production of compound [1d] corresponding to formula [1] wherein $R^1$ is alkoxycarbonylamino and $R^2$ is $NH_2$)

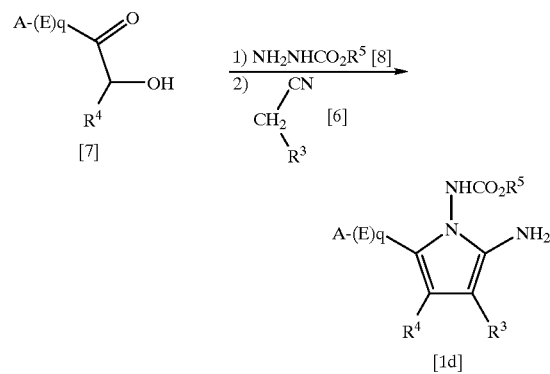

[In the above reaction schema, A, E, q, $R^3$, $R^4$, and $R^5$ are as defined hereinbefore]

Compound [1d] can be synthesized by reacting compound [7] with compound [8] and subjecting the reaction product further to reaction with compound [6].

Except that compound [6] is used in lieu of compound [4], the reaction can be carried out in the similar manner as in Synthetic Process C.

Starting with the compound [1f] corresponding to compound [1] of the invention wherein $R^2$ is $NH_2$, which is synthesized by the above Synthetic Processes A–E, the compound in which $R^2$ is alkyl-substituted amino can be synthesized by the following Synthetic Process F or Synthetic Process G.

Synthetic Process F (production of compound [1g] corresponding to formula [1] wherein $R^2$ is monoalkylamino and compound [1h] corresponding to formula [1] wherein $R^2$ is dialkylamino)

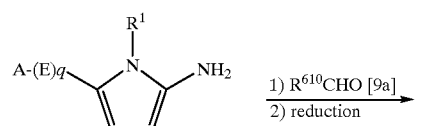

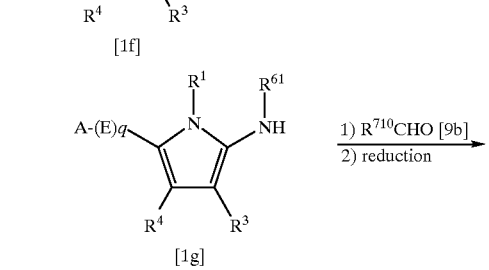

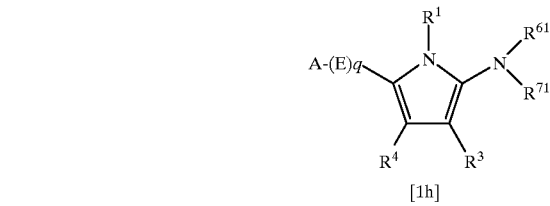

[In the above reaction schemes, A, E, q, $R^1$, $R^3$, and $R^4$ are as defined hereinbefore. $R^{61}$ and $R^{71}$ may be the same or different and each represents alkyl such as that mentioned hereinbefore (which alkyl may be substituted by (1) hydroxy, (2) aryl which may be substituted by alkoxy, or (3) aromatic heterocyclyl). $R^{610}$ and $R^{710}$ represent residues available upon elimination of the bonding-end —$CH_2$— from $R^{61}$ and $R^{71}$, respectively]

Compound [1g] can be synthesized by reacting compound [1f] with aldehyde [9a] and then reducing the reaction product. Compound [1h] can be synthesized from compound [1g] and aldehyde [9b] in the similar manner.

The reaction of compound [1f] with aldehyde [9a] can be generally carried out in the absence of a solvent or in a solvent which does not interfere with the reaction (e.g. ethers such as tetrahydrofuran (THF) and diethyl ether, halogenated hydrocarbons such as chloroform and methylene chloride, hydrocarbons such as benzene, toluene and n-hexane, polar solvents such as acetonitrile, N,N-dimethylformamide (DMF) and dimethyl sulfoxide (DMSO), and mixture of such solvents), either in the presence of a dehydrating agent (e.g. magnesium sulfate, sodium sulfate, active calcium sulfate, molecular sieves) or in the absence of the dehydrating agent, at 0–150° C. The reaction time is dependent on the species of compound [1f] and aldehyde [9a] and the reaction temperature but may generally range from 30 minutes to 120 hours. The molar ratio of aldehyde [9a] to compound [1f] is generally 1–1.2:1.

The reduction reaction can be carried out using a reducing agent such as sodium borohydride or sodium cyanoborohydride in a solvent which does not interfere with the reaction (e.g. methanol, ethanol, isopropanol, DMF, DMSO, acetonitrile, or ethyl acetate, or a mixture thereof) at −10 to 40° C. The reaction time is dependent on the species of compound [1f], aldehyde [9a], and reducing agent used and the reaction temperature but may generally range from 30 minutes to 24 hours. The proportion of the reducing agent is generally 1–10 moles per mole of compound [1f].

In carrying out this synthetic process, an orthoformic ester (e.g. methyl orthoformate, ethyl orthoformate) can be used in lieu of formaldehyde (compound [9a] ($R^{610}$=H), compound [9b] ($R^{710}$=H).

Synthetic Process G (production of compound [1i] corresponding to formula [1] wherein $R^2$ is 2-oxocyclic amino (Y is —$CH_2$—))

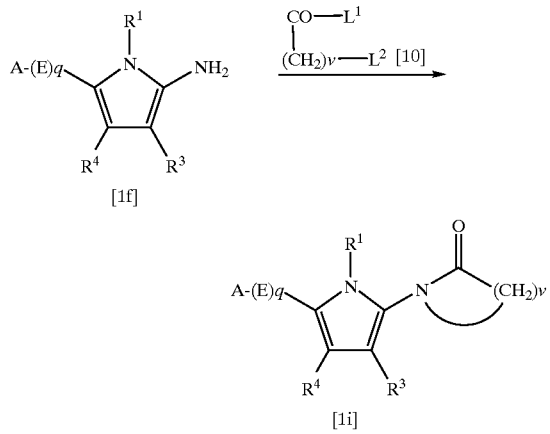

[In the above reaction schema, A, E, q, $R^1$, $R^3$, and $R^4$ are as defined hereinbefore; $L^1$ and $L^2$ may be the same or different and each represents halogen such as chlorine, bromine, or iodine; v represents an integer of 3–5.

Compound [1i] can be produced by reacting compound [1f] with compound [10].

In this reaction, the acyl halide moiety of compound [10] undergoes reaction in the first place and the alkyl halide moiety then undergoes reaction.

The reaction of the acyl halide moiety can be generally carried out in a solvent which does not interfere with the reaction (e.g. ethers such as tetrahydrofuran (THF) and diethyl ether, halogenated hydrocarbons such as chloroform and methylene chloride, hydrocarbons such as benzene, toluene and n-hexane, polar solvents such as acetonitrile, N,N-dimethylformamide (DMF), dimethyl sulfoxide (DMSO), and mixture of such solvents) in the presence of a base (e.g. sodium hydrogen carbonate, potassium hydrogen carbonate, potassium carbonate, sodium carbonate, pyridine, 4-dimethylaminopyridine, triethylamine) at −78 to 100° C. The reaction time is dependent on the species of compound [1f] and compound [10] and the reaction temperature but may generally range from 30 minutes to 24 hours. The molar ratio of compound [10] to compound [1f] is 1–1.2:1. The proportion of the base is generally 1–10 moles per mole of compound [1f].

The reaction of the alkyl halide moiety is carried out using the compound obtained in the previous step and a strong base (e.g. potassium tert-butoxide, sodium methoxide, sodium ethoxide, sodium hydride) in a solvent which does not interfere with the reaction (e.g. alcohols such as methanol and ethanol, ethers such as tetrahydrofuran (THF) and diethyl ether, halogenated hydrocarbons such as chloroform and methylene chloride, hydrocarbons such as benzene, toluene and n-hexane, polar solvents such as acetonitrile, N,N-dimethylformamide (DMF), dimethyl sulfoxide (DMSO), and mixture of such solvents) at 0–100° C. The reaction time is dependent on the species of compound [1f] and compound [10] and the reaction temperature but may generally range from 30 minutes to 24 hours. The proportion of the strong base is generally 1–1.2 molar equivalents based on compound [1f].

Synthetic Process H (production of compound [1j] corresponding to formula [1] wherein $R^1$ is hydrogen, $R^2$ is (1) alkyl, (2) aryl which may be substituted, or (3) aromatic heterocyclyl which may be substituted, and $R^4$ is hydrogen)

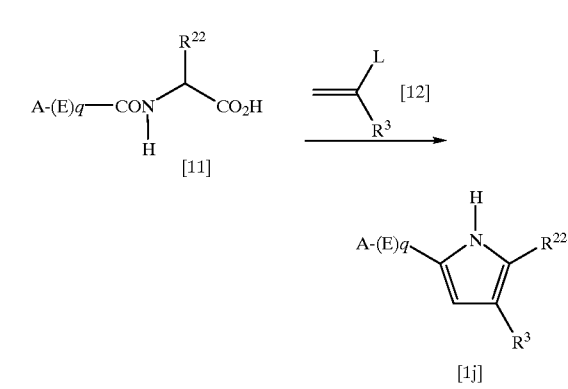

[In the above reaction schema, A, E, q, $R^3$, and L are as defined hereinbefore; $R^{22}$ represents (1) alkyl such as that defined hereinbefore, (2) optionally substituted aryl such as that defined hereinbefore, or (3) optionally substituted aromatic heterocyclyl such as that defined hereinbefore]

Compound [1j] can be synthesized by reacting compound [11] with compound [12] in the presence of an acid anhydride (e.g. acetic anhydride, propionic anhydride, an anhydride of A—$(E)_q$—$CO_2H$).

This reaction is generally carried out using the above-mentioned acid anhydride as a solvent at 0–160° C. The reaction time is dependent on the species of compound [11] and compound [12] and the reaction temperature but may generally range from 5 minutes to 24 hours. The molar ratio of compound [12] to compound [11] is generally 10–20:1. The proportion of said acid anhydride is generally 10–100 moles per mole of compound [11].

Synthetic Process I (production of compound [1k] corresponding to formula [1] wherein $R^2$ is (1) alkyl, (2) aryl which may be substituted, or (3) aromatic heterocyclyl which may be substituted, and $R^3$ is cyano)

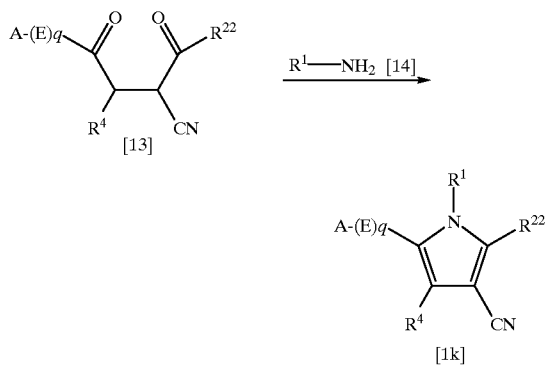

[In the above reaction schema, A, E, q, $R^1$, $R^4$, and $R^{22}$ are as defined hereinbefore]

Compound [1k] can be synthesized by reacting compound [13] with either compound [14] or its acid addition salt.

This reaction can be generally carried out in a solvent which does not interfere with the reaction (e.g. alcohols such as methanol, ethanol, n-propanol, isopropanol, n-butanol, and tert-butanol, ethers solvent such as tetrahydrofuran (THF) and diethyl ether, halogenated hydrocarbons such as chloroform and methylene chloride, hydrocarbons such as benzene, toluene and n-hexane, polar solvents such as acetonitrile, N,N-dimethylformamide (DMF), dimethyl sulfoxide (DMSO), and mixture of such solvents), either in the presence of an acid catalyst (e.g. acetic acid, p-toluenesulfonic acid) or in the absence of the acid, at 20–160° C. The reaction time is dependent on the species of compound [13] and compound [14] and the reaction temperature but may generally range from 5 minutes to 18 hours. The molar ratio of compound [14] to compound [13] is generally 1–5:1. The proportion of the acid catalyst is generally 0.1–2 moles per mole of compound [13]. The acid catalyst (such as acetic acid) may be used in excess so that it may function as the solvent as well.

Referring to species of compound [1] wherein $R^3$ is cyano, this $R^3$ can be converted to carbamoyl by the known procedure.

With regard to species of compound [1] wherein $R^2$ and A respectively represent nitro-substituted aryl or nitro-substituted aromatic heterocyclyl, the nitro can be converted to amino by the known procedure.

Compound [1] can be isolated and purified from the reaction mixture by conventional separation-purification techniques such as extraction, concentration, neutralization, filtration, recrystallization, column chromatography, thin-layer chromatography, and ion exchange chromatography as used selectively in a suitable combination.

Any species of compound [1] of the invention that is basic can be used in the form of a free base as a medicine but may be converted to a pharmaceutically acceptable salt by the per se known method and used as such. The salt includes salts with mineral acids such as hydrochloric acid, hydrobromic acid, sulfuric acid and phosphoric acid and salts with organic acids such as acetic acid, citric acid, tartaric acid, maleic acid, succinic acid, fumaric acid, p-toluenesulfonic acid, benzenesulfonic acid and methanesulfonic acid.

The hydrochloride, for instance, can be obtained by dissolving compound [1] in alcoholic hydrochloric acid.

There are cases in which a solvate (inclusive of hydrate) of the compound [1] or salt of the invention is available upon recrystallization of the solvated compound from the corresponding solvent or an appropriate solvent mixture containing the corresponding solvent. Such solvates also fall within the scope of the invention.

For instance, there is the case that the hydrate of compound [1] according to the invention is obtained upon recrystallization of compound [1] from an aqueous alcohol.

Compound [1] of the invention may show polymorphism and in such cases the respective polymorphs also fall within the scope of the invention.

The compound [3] through compound [14], which are used as starting compounds in the production of compound [1] of the invention are either known compounds or compounds which can be prepared by the similar process to per se known processes as described in Reference Examples which appear hereinafter.

The compound of the invention is useful as a medicine. As can be understood from the Test Examples presented hereinafter, the compound of the invention has potent bladder capacity increasing activity and is useful particularly as a therapeutic drug for pollakiuria or urinary incontinence.

In the administration of the compound of the invention as a medicine, the compound can be administered either as it is or in the form of a pharmaceutical composition containing 0.1–99.5%, preferably 0.5–90%, of the compound in a pharmaceutically acceptable, nontoxic and inert carrier, to animals including humans.

The carrier includes solid, semisolid or liquid diluents, fillers and other formulation auxiliaries and they may be used either solely or jointly. The pharmaceutical composition is preferably administered in unit dosage forms. The pharmaceutical composition of the invention can be administered intravenously, orally, into the tissue, topically (e.g. transdermally), or rectally. Of course, the dosage form suited to each route of administration should be selected. Oral administration is particularly advantageous.

The dosage of the pharmaceutical composition of the invention for the treatment of pollakiuria or urinary incontience is preferably established in consideration of patient factors, e.g. age and body weight, route of administration, nature and severity of disease, etc. Usually, however, the daily dose as an effective amount of the compound of the invention for adult patients is 0.1–1000 mg/patient, preferably 1–500 mg/patient.

Lower doses may be sufficient in some cases and higher doses may be needed in other cases. The above dosage may be administered in 2–3 divided doses a day.

BEST MODE FOR CARRYING OUT THE INVENTION

The following Examples, Test Examples and Formulation Examples for the pharmaceutical composition of the invention are further illustrative of the present invention.

REFERENCE EXAMPLE 1

2-Bromo-2',5'-difluoropropiophenone

To a solution of 2',5'-difluoropropiophenone (2.12 g) in diethyl ether (20 ml) under ice-cooling was added bromine dropwise, and the mixture was stirred at room temperature overnight. To this reaction mixture was added ice and the diethyl ether layer was separated, followed by washing with water and saturated aqueous solution of sodium hydrogen carbonate in that order and dried over anhydrous magnesium sulfate ($MgSO_4$). The ether layer was concentrated under reduced pressure to provide the title compound.

The following compounds were synthesized by substantially the same procedure as Reference Example 1.

2-Bromo-4'-ethoxyacetophenone,
Bromomethyl 3-thienyl ketone,
2-Bromo-3',4'-methylenedioxyacetophenone,
2-Bromo-2',4'-difluoroacetophenone,
2-Bromo-2',5'-difluoroacetophenone,
2-(Bromoacetyl)benzofuran,
2-Bromo-4'-methanesulfonamidoacetophenone,
2-Bromoacetophenone,
2-Bromo-4'-methoxyacetophenone,
2-Bromo-4'-chloroacetophenone,
2-Bromo-4'-bromoacetophenone,
2-Bromo-4'-nitroacetophenone,
2-Bromo-4'-methylacetophenone,
2-Bromo-3'-methoxyacetophenone,
2-Bromo-2'-methoxyacetophenone,
Bromoethyl 2-thienyl ketone,
2-Bromo-3'-ethoxyacetophenone,
2-Bromo-4'-phenylacetophenone,
2-Bromo-3',4'-dichloroacetophenone,
2-Bromo-4'-fluoroacetophenone,
3-(Bromoacetyl)pyridine,
2-Bromo-4'-isopropoxyacetophenone,
2-(Bromoacetyl)naphthalene,
2-Bromo-3'-chloroacetophenone,
2-Bromo-3'-methyl-4'-chloroacetophenone,
2-(Bromoacetyl)pyridine,
Bromoacetone,
(1-Bromoethyl)methyl ketone,
2-Bromo-4'-n-propoxyacetophenone,
2-Bromo-4'-(2-methoxyethoxy)acetophenone,
2-Bromo-4'-(2-ethoxyethoxy)acetophenone,
2-Bromo-4'-benzyloxyacetophenone,
2-Bromo-2'-fluoroacetophenone,
2-Bromo-3'-fluoroacetophenone,
2-Bromo-4'-trifluoromethylacetophenone,
2-Bromo-2'-trifluoromethylacetophenone,
2-Bromo-3'-(2-methoxyethoxy)acetophenone,
2-(Bromoacetyl)furan,
2-Bromo-3'-fluoro-4'-methoxyacetophenone,
2-Bromo-2'-fluoro-4'-metoxyacetophenone,
2-Bromo-4'-(2-fluoroethoxy)acetophenone,
2-Bromo-3'-(2-fluoroethoxy)acetophenone,
2-Bromo-5'-bromo-2',4'-diethoxypropiophenone,
2-Bromo-2'-ethoxypriopiophenone,
2-Bromo-4'-isopropoxypropiophenone,
2-Bromo-3',5'-ditrifluoromethylpropiophenone,
2-Bromo-2'-fluoropropiophenone,
2-Bromopropiophenone,
2-Bromo-4'-fluoropropiophenone,
2-Bromo-3'-nitropropiophenone,
2-Bromo-3'-chloropropiophenone,
2-Bromo-4'-methylpropiophenone,
2-Bromo-3'-nitropropiophenone,
2-Bromo-2',5'-dichloropropiophenone,
2-Bromo-3'-nitropropiophenone,
2-Bromo-1-(2-pyridyl)-1-propanone,
2-Bromo-1-(2-naphthyl)-1-propanone,
2-Bromo-4'-methoxypropiophenone,
2-Bromo-1-(3-pyridyl)-1-propanone,
2-Bromo-1-(2-thienyl)-1-propanone,
2-Bromo-3',4'-dichloropropiophenone,
2-Bromo-4'-chloropropiophenone,
2-Bromo-4'-bromopropiophenone,
2-Bromo-4'-benzyloxypropiophenone,
2-Bromo-4'-ethoxypropiophenone,
2-Bromo-4'-hydroxypropiophenone,
2-Bromo-2',5'-dimethoxypropiophenone,
2-Bromo-3'-bromopropiophenone,
2-Bromo-3'-chloropropiophenone,
2-Bromo-2'-methoxypropiophenone,
2-Bromo-3',4'-methylenedioxypropiophenone,
2-Bromo-2',4'-dichloropropiophenone,
2-Bromo-1-(2-furyl)-1-propanone,
2-Bromo-1-(4-pyridyl)-1-propanone,
3-Bromo-4-chromanone,
2-Bromo-2'-chloropropiophenone,
2-Bromo-2'-methoxypropiophenone,
2-Bromo-2',5'-difluoropropiophenone,
2-Bromo-2'-methylpropiophenone,
2-Bromo-2',6'-difluoropropiophenone,
2-Bromo-4'-trifluoromethylpropiophenone,
2-Bromo-3'-trifluoromethylpropiophenone,
2-Bromo-3'-methoxycarbonylpropiophenone,
2-Bromo-5'-fluoro-2'-methoxypropiophenone.

REFERENCE EXAMPLE 2

2-Cyanoacetamidine

To saturated ammonia/ethanol (20 ml) was added ethyl 2-cyanoacetimidate hydrochloride (3.7 g) under ice-cooling, and the mixture was stirred at the same temperature for 0.5 hour and then at room temperature for 2 hours. The precipitated was filtered off and the filtrate was concentrated under reduced pressure on a water bath to remove the excess ammonia. The residue was used as it was in the next reaction.

REFERENCE EXAMPLE 3

3-Amino-3-morpholinoacrylonitrile

In anhydrous ethanol (10 ml) was dissolved ethyl 2-cyanoacetimidate (1.0 g), followed by addition of morpholine (0.78 g). The mixture was stirred at room temperature for 4 hours, and the separated crystals were collected by filtration. This crystal crop was used as it was in the next reaction.

REFERENCE EXAMPLE 4

Carbamoylacetamidine

The title compound was synthesized by the known process (J. Amer. Chem. Soc., 73, 2760, 1951).

REFERENCE EXAMPLE 5

1-(2-Fluorophenyl)-1-acetamido-2-propanone

A mixture of 2-fluorophenylglycine (5.0 g), pyridine (15.6 g), and acetic anhydride (25.7 g) was heated at 140–150° C.

for 4 hours. This reaction mixture was concentrated under reduced pressure and the residue was diluted with diethyl ether. The ether layer was washed with water and a saturated aqueous solution of sodium hydrogen carbonate. The ether layer was dried over $MgSO_4$ and concentrated under reduced pressure. The residue was purified by silica gel column chromatography (eluent: n-hexane/ethyl acetate) to provide the title compound as yellow oily substance (4.7 g).

The following compounds were synthesized in the similar manner as described in Reference Example 5.

1-Phenyl-1-acetamido-2-propanone,
1-(4-Fluorophenyl)-1-acetamido-2-propanone,
3-Acetamido-2-butanone,
1-(3-Nitrophenyl)-1-acetamido-2-propanone,
4-Phenyl-3-acetamido-2-butanone,
1-Phenyl-1-propanamido-2-butanone,
4-(4-Hydroxyphenyl)-3-acetamido-2-butanone,
1-Phenyl-1-isobutanamido-3-methyl-2-butanone,
2-Propanamido-3-pentanone,
4-(Indol-3-yl)-3-acetamido-2-butanone,
1-(3-Chlorophenyl)-1-acetamido-2-propanone
1-Phenyl-1-butanamido-2-pentanone,
3-Acetamido-2-pentanone,
4-(4-Chlorophenyl)-3-acetamido-2-butanone,
1-(3-Pyridyl)-1-acetamido-2-propanone,
1-(2,5-Dichlorophenyl)-1-acetamido-2-propanone,
1-(2-Pyridyl)-1-acetamido-2-propanone,
1-(2-Naphthyl)-1-acetamido-2-propanone,
1-(4-Methoxyphenyl)-1-acetamido-2-propanone.

REFERENCE EXAMPLE 6

1,1-Dicyano-2-phenyl-2-(1-bromoethyl)ethylene

Propiophenone (30 g) and malononitrile (15 g) were added to benzene (100 ml), followed by addition of acetic acid (5.45 g) and ammonium acetate (1.8 g), the mixture was refluxed for 8 hours, while the byproduct water was continuously distilled off. After cooling to room temperature, the reaction mixture was washed with water, dried over $MgSO_4$, and concentrated under reduced pressure. The residual black oily substance was subjected to vacuum distillation to provide a pale yellow oily substance (32.5 g) (b.p. 120–125° C./2–3 mmHg).

The obtained compound (3.6 g) was dissolved in anhydrous benzene (30 ml), followed by addition of N-bromosuccinimide (3.6 g) and benzoyl peroxide (a catalyst amount), and the mixture was refluxed for 14 hours. After cooling to room temperature, the reaction mixture was filtered to remove insoluble matter and the filtrate was distilled under reduced pressure to remove the solvent. The residual tan oily substance was recrystallized from ethanol to provide the title compound as light-yellow crystals (2.99 g).

REFERENCE EXAMPLE 7

Sodium cyanoacetone enolate

A solution of 5-methylisoxazole (16.6 g) in ethanol was added dropwise to a solution of sodium ethoxide in ethanol (prepared from 4.6 g of sodium metal and 150 ml of ethanol) under ice-cooling. After completion of dropwise addition, the mixture was stirred at room temperature for 2 hours.

Then, ether (150 ml) was added thereto and the mixture was further stirred for several minutes under ice-cooling. The sodium salt was then collected by filtration, washed with ether, and dried in vacuo to provide the title compound as colorless powder (18.1 g).

REFERENCE EXAMPLE 8

2-Acetyl-3-(2-fluorobenzoyl)butyronitrile

To a solution of 2-bromo-2'-fluoropropiophenone (3.45 g) in ethanol (40 ml) was added a solution of sodium cyanoacetone enolate (1.57 g), as obtained in Reference Example 7, in ethanol (15 ml) dropwise under ice-cooling and the mixture was stirred for 18 hours. The solvent was then distilled off under reduced pressure and the resulting residue was dissolved in ethyl acetate. This solution was washed with water and dried over $MgSO_4$, and the solvent was distilled off under reduced pressure. The resulting residual oily substance was purified by silica gel column chromatography [Wakogel C-200, 110 g; eluent: ethyl acetate/n-hexane (4:1)] to provide the title compound as yellow oily substance (1.43 g).

The following compounds were synthesized in the similar manner as described in Reference Example 8.

2-Acetyl-3-benzoylbutyronitrile
2-Acetyl-3-(3-isopropoxybenzoyl)propionitrile,
2-Acetyl-3-(4-trifluoromethoxybenzoyl)propionitrile,
2-Acetyl-3-(3-trifluoromethylbenzoyl)propionitrile,
2-Acetyl-3-(3-trifluoromethoxybenzoyl)propionitrile,
2-Acetyl-3-[4-(2-methoxy)ethoxybenzoyl]propionitrile,
2-Acetyl-3-(2-fluorobenzoyl)propionitrile,
2-Acetyl-3-(benzofuran-2-carbonyl)propionitrile,
2-Acetyl-3-(3,4-methylenedioxybenzoyl)propionitrile,
2-Acetyl-3-(2,5-difluorobenzoyl)propionitrile,
2-Acetyl-3-(4-chloro-3-methylbenzoyl)propionitrile,
2-Acetyl-3-(2-naphthoyl)propionitrile,
2-Acetyl-3-(3-bromobenzoyl)propionitrile
2-Acetyl-3-(3-chloro-4-methylbenzoyl)butyronitrile,
2-Acetyl-3-(4-fluorobenzoyl)propionitrile,
2-Acetyl-3-(4-methanesulfonylaminobenzoyl) propionitrile,
2-Acetyl-3-(2-furoyl)butyronitrile,
2-Acetyl-3-(3-chlorobenzoyl)butyronitrile,
2-Acetyl-3-(3-methoxybenzoyl)propionitrile.

EXAMPLE 1

2-Amino-3-cyano-4-methyl-5-(2,5-difluorophenyl) pyrrole (compound No. 63)

To an ethanolic solution of 2-cyanoacetamidine obtained from ethyl 2-cyanoacetimidate hydrochloride (3.7 g) as in Reference Example 2, was added a solution of 2-bromo-2', 5'-difluoropropiophenone (3.7 g) in ethanol dropwise under ice-cooling with stirring, and the mixture was further stirred at room temperature overnight. This reaction mixture was poured into iced water and the separated crystal crop was collected by filtration. This crude product was dissolved in ethyl acetate. The ethyl acetate layer was washed with water, dried over $MgSO_4$ and concentrated under reduced pressure. The residue was purified by silica gel column chromatography (Wakogel C-200, 200 g; eluent: chloroform) and recrystallized from benzene-n-hexane to provide the title compound as yellow powder (0.58 g). m.p. 146–147° C.

Elemental analysis ($C_{12}H_9F_2N_3$)

Calcd. (%): C, 61.80; H, 3.89; N, 18.02

Found (%): C, 61.71; H, 3.91; N, 17.69

EXAMPLE 2

3-Cyano-5-(4-fluorophenyl)-4-methyl-2-morpholinopyrrole (compound No. 72)

In anhydrous ethanol (10 ml) was dissolved 3-amino-3-morpholinoacrylonitrile, as prepared from ethyl 2-cyanoacetimidate (1.0 g) and morpholine (0.78 g) as in Reference Example 3, followed by addition of sodium hydrogen carbonate (0.95 g). Then, a solution of 2-bromo-4′-fluoropropiophenone (2.06 g) in ethanol was added dropwise thereto at room temperature with stirring. The mixture was refluxed for 10 minutes and, then, stirred at room temperature overnight. The separated crystal crop was collected by filtration and recrystallized from ethanol to provide the title compound as colorless crystals (0.12 g). m.p. 245–247° C.

Elemental analysis ($C_{16}H_{16}FN_3O$)

Calcd. (%): C, 67.35; H, 5.65; N, 14.73

Found (%): C, 67.14; H, 5.86; N, 14.69

EXAMPLE 3

2-Amino-3-cyano-4H-[1]benzopyrano[4,3-b]pyrrole (compound No. 52)

To an ethanolic solution of 2-cyanoacetamidine prepared from ethyl 2-cyanoacetimidate hydrochloride (4.0 g) as in Reference Example 2 was added a solution of 3-bromo-4-chromanone (3.0 g) in ethanol dropwise under ice-cooling with stirring. The mixture was stirred at room temperature overnight and, then, concentrated under reduced pressure. The resulting crude product was dissolved in ethyl acetate. The ethyl acetate layer was washed with water, dried over $MgSO_4$ and concentrated under reduced pressure. The residue was purified by silica gel column chromatography (Wakogel C-200, 200 g; eluent: 2% methanol/chloroform) and recrystallized from acetone/isopropyl ether to provide the title compound as light-brown crystals (0.31 g). m.p. 216–217° C.

Elemental analysis ($C_{12}H_9N_3O$)

Calcd. (%): C, 68.24; H, 4.29; N, 19.89

Found (%): C, 68.29; H, 4.52; N, 19.81

EXAMPLE 4

2-Amino-3-carbamoyl-4-methyl-5-phenylpyrrole (compound No. 76)

To a solution (20 ml) of carbamoylacetamidine (5.1 g) in ethanol was added a solution of 2-bromopropiophenone (4.0 g) in ethanol dropwise thereto under ice-cooling with stirring and the mixture was then stirred at room temperature overnight. The insoluble matter was filtered off and the filtrate was concentrated under reduced pressure. The obtained product was washed with benzene, purified by silica gel column chromatography (Wakogel C-200, 200 g; eluent: 50% ethyl acetate/n-hexane), and recrystallized from ethyl acetate/diethyl ether to provide the title compound as colorless crystals (0.2 g). m.p. 195–197° C.

Elemental analysis ($C_{12}H_{13}N_3O$)

Calcd. (%): C, 66.96; H, 6.09; N, 19.52

Found (%): C, 66.95; H, 6.23; N, 19.38

EXAMPLE 5-(1)

2-Amino-3-cyano-4-methyl-5-(2-fluorophenyl) pyrrole (compound No. 1)

1-(2-Fluorophenyl)-1-acetamido-2-propanone (3.13 g) and malononitrile (1.49 g) were dissolved in methanol (15 ml) and the solution was stirred under ice-cooling. Then, 55% aqueous solution of potassium hydroxide was added to the above solution to adjust to pH 10. The reaction mixture was then warmed and stirred at 55–60° C. for 0.5 hour. After cooling, the reaction mixture was poured into iced water and the resulting crystals were collected by filtration. This crude crystalline product was recrystallized from methanol-water and, further, from benzene to provide the title compound as colorless crystals (0.72 g). m.p. 117–118° C.

Elemental analysis ($C_{12}H_{10}FN_3$)

Calcd. (%): C, 66.97; H, 4.68; N, 19.52

Found (%): C, 67.09; H, 4.74; N, 19.40

EXAMPLE 5-(2)

2-Amino-3-cyano-4-methyl-5-(2-fluorophenyl) pyrrole (compound No. 1: an alternative process)

To an ethanolic solution of 2-cyanoacetamidine prepared from 10 g of ethyl 2-cyanoacetimidate hydrochloride as in Reference Example 2 was added a solution of 2-bromo-2′-fluoropropiophenone (7.6 g) in ethanol dropwise under ice-cooling with stirring, and the mixture was then stirred at room temperature overnight. This reaction mixture was poured into iced water (500 g) and the resulting crystals were collected by filtration. The crude crystal crop was washed well with n-hexane, air-dried, and purified by flash chromatography (Kieselgel 60H, 90 g; eluent: 30% ethyl acetate/n-hexane). Recrystallization from benzene-n-hexane (1:1) yielded the title compound as colorless crystals (4.67 g). The physical constants of this product were in agreement with those of the product obtained in Example 5-(1).

EXAMPLE 6

2-Amino-3-cyano-1-methoxycarbonylamino-4-methyl-5-phenylpyrrole (compound No. 13)

In anhydrous ethanol (30 ml) was suspended 1,1-dicyano-2-phenyl-2-(1-bromoethyl)ethylene (1.3 g) and while the suspension was stirred at 65° C., 10 ml of a suspension of methyl hydrazinecarboxylate (1.3 g) in anhydrous ethanol was added dropwise over about 5 minutes. The mixture was stirred at the same temperature for 4.5 hours and poured in iced water (200 g), and, the resulting crystals were collected by filtration. The resulting crystals (1.0 g) were purified by silica gel column chromatography (Wakogel C-200, 200 g; eluent; 30% ethyl acetate/n-hexane) and recrystallized from ethyl acetate/isopropyl ether to provide the title compound as colorless needles (0.48 g). m.p. 178–179° C.

Elemental analysis ($C_{14}H_{14}N_4O_2$)

Calcd. (%): C, 62.21; H, 5.22; N, 20.73

Found (%): C, 62.25; H, 4.92; N, 20.72

EXAMPLE 7

3-Cyano-4-methyl-2-methylamino-5-phenylpyrrole (compound No. 75)

2-Amino-3-cyano-4-methyl-5-phenylpyrrole (compound No. R1) (3.0 g), prepared in the process described in the literature (J. Prakt. Chem., 318, 663, 1976), and ethyl orthoformate (12 ml) were refluxed for 4.5 hours. After cooling the reaction mixture to room temperature, the crystals which had separated out were collected by filtration. This crystal crop was washed with benzene and then petroleum ether, air-dried, and purified by silica gel column chromatography (Wakogel C-200, 200 g; eluent: chloroform) to obtain the iminoether as light-green crystals (1.9 g). This iminoether (1.85 g) was dissolved in anhydrous methanol (37 ml) and while the solution was stirred under ice-cooling, sodium borohydride (0.33 g) was added thereto in small portions. The mixture was stirred under cooling with water for 12 hours, after which the insoluble matter was removed by filtration and washed with benzene. The filtrate and washes were combined and concentrated under reduced pressure and the resulting residue was purified by silica gel column chromatography (Wakogel C-200, 200 g; eluent: chloroform) and recrystallized from benzene/n-hexane to provide the title compound as pale yellow crystals (0.37 g). m.p. 138–139° C.

Elemental analysis ($C_{13}H_{13}N_3$)

Calcd. (%): C, 73.91; H, 6.20; N, 19.89

Found (%): C, 73.85; H, 6.52; N, 19.66

EXAMPLE 8

2-Benzylamino-3-cyano-4-methyl-5-(2-fluorophenyl)pyrrole (compound No. 74)

To a solution of 2-amino-3-cyano-4-methyl-5-(2-fluorophenyl)pyrrole (Compound No. 1) obtained in Example 5 (0.21 g) in methylene chloride (5 ml) was added a small amount of magnesium sulfate and the mixture was stirred under ice-cooling. Then, a solution of benzaldehyde (0.11 g) in methylene chloride (5 ml) was added dropwise at the same temperature and the mixture was stirred at room temperature for 5 days. The magnesium sulfate was then filtered off and the filtrate was concentrated under reduced pressure. After the residue was dissolved in methanol (15 ml), sodium borohydride (76 mg) was added thereto under ice-cooling. This mixture was stirred at room temperature for 1 hour and the reaction mixture was concentrated under reduced pressure. To the residue was added ethyl acetate, and the ethyl acetate layer was washed with water, dried over $MgSO_4$, and concentrated under reduced pressure. The residue was purified by silica gel column chromatography (Wakogel C-200, 50 g; eluent: chloroform/methanol=50/1) and the resulting crystals were recrystallized from benzene/n-hexane to provide the title compound as light-yellow powder (0.17 g). m.p. 151–152° C.

Elemental analysis ($C_{19}H_{16}FN_3$)

Calcd. (%): C, 74.74; H, 5.28; N, 13.76

Found (%): C, 74.78; H, 5.38; N, 13.50

EXAMPLE 9

3-Cyano-4-methyl-2-(2-oxopyrrolidin-1-yl)-5-phenylpyrrole (compound No. 73)

To a solution of 3-cyano-4-methyl-2-amino-5-phenylpyrrole (4.9 g) in THF (80 ml) was added triethylamine (2.5 g) and while the mixture was stirred at −50° C., 4-chlorobutyryl chloride (3.5 g) was added. This reaction mixture was then stirred at room temperature for 1.5 hours, after which the insoluble matter was filtered off. The filtrate was diluted with ethyl acetate and the organic layer was washed with water and saturated aqueous solution of sodium hydrogen carbonate, dried over $MgSO_4$, and concentrated under reduced pressure. The residue was recrystallized from benzene/n-hexane. The crystals were suspended in ethanol (40 ml), and potassium tert-butoxide (1.32 g) was added thereto. The mixture was stirred at room temperature overnight and the resulting crystals were collected by filtration, washed with water, and air-dried. The crude crystals thus obtained were recrystallized from ethanol to provide the title compound as light-yellow needles (1.5 g). m.p. 140–141° C.

Elemental analysis ($C_{16}H_{15}N_3O$)

Calcd. (%): C, 72.43; H, 5.70; N, 15.84

Found (%): C, 72.42; H, 5.64; N, 15.79

EXAMPLE 10

2-Amino-3-cyano-4-methyl-5-(3-pyridyl)pyrrole hydrochloride (compound No. 14)

2-Amino-3-cyano-4-methyl-5-(3-pyridyl)pyrrole (compound No. 8) obtained in the same manner as Example 1 (5.0 g) was dissolved in methanol (220 ml) under heating, followed by addition of 40% HCl-methanol (4 ml) under ice-cooling with stirring. The separated crystals were collected by filtration, washed with methanol (50 ml) twice and diethyl ether (50 ml) 3 times, and air-dried. The crude crystals thus obtained were recrystallized from methanol to provide the title compound as reddish brown crystals (3.4 g). m.p. 279–281° C.

Elemental analysis ($C_{11}H_{10}N_4 \cdot HCl$)

Calcd. (%): C, 56.30; H, 4.72; N, 23.89

Found (%): C, 56.08; H, 4.80; N, 23.90

EXAMPLE 11

5-(3-Chlorophenyl)-3-cyano-2-methylpyrrole (compound No. 84) and 2-(3-chlorophenyl)-3-cyano-5-methylpyrrole (compound No. 83)

N-(3-chlorobenzoyl)alanine (3.5 g) and 2-chloroacrylonitrile (13.3 g) were dissolved in acetic anhydride (100 ml) and the solution was stirred at 80° C. for 5 hours. This reaction mixture was concentrated under reduced pressure and the residue was subjected to silica gel column chromatography (Wakogel C-200, 600 g; eluent:methylene chloride) to fractionate the objective compounds. The compounds were respectively recrystallized from benzene/n-hexane.

Compound No. 84 was obtained as light-brown powder (291 mg). m.p. 208–209° C.

Elemental analysis ($C_{12}H_9ClN_2$)

Calcd. (%): C, 66.52; H, 4.19; N, 12.93

Found (%): C, 66.47; H, 4.21; N, 12.87

Compound No. 83 was obtained as colorless scales (426 mg). m.p. 189–190° C.

Elemental analysis ($C_{12}H_9ClN_2$)

Calcd. (%): C, 66.52; H, 4.19; N, 12.93

Found (%): C, 66.51; H, 4.24; N, 12.86

EXAMPLE 12

5-(2-Fluorophenyl)-3-cyano-2,4-dimethylpyrrole (compound No. 194)

To a solution of 2-acetyl-3-(2-fluorobenzoyl)butyronitrile (1.4 g) obtained in Reference Example 8 in acetic acid (15 ml) was added ammonium acetate (6.0 g) and the mixture was stirred at 90° C. for 15 minutes. This reaction mixture was poured in iced water and the resulting crystals were collected by filtration. This crystal crop was dissolved in benzene and dried over MgSO$_4$ and the solvent was distilled off under reduced pressure. The residual orange-colored crystals were purified by silica gel column chromatography (Wakogel C-200, 120 g; eluent:chloroform) and the resulting orange-colored powder was recrystallized from benzene/n-hexane to provide the title compound as orange-colored colorless needles (0.36 g) m.p. 125–127° C.

Elemental analysis (C$_{13}$H$_{11}$FN$_2$)
Calcd. (%): C, 72.88; H, 5.18; N, 13.08
Found (%): C, 73.11; H, 5.39; N, 13.08

The structural formulas and physicochemical properties of the compounds synthesized in Examples 1–12 and the compounds synthesized in the similar procedures as the Examples (compound Nos. 2–12, 15–51, 53–62, 64–71, 77–82, 85–193, 195–266) are listed in Table 2. However, the present invention is by no means limited to those compounds.

In the column "Synthetic process" of the table, synthetic processes used for the production of the respective compounds are indicated as "A"–"I". "A and B", for instance, in the column means that the same compound was synthesized by both synthetic process A and synthetic process B.

TABLE 2

| Compound No. | Structural formula | m.p. (° C.) State | Molecular formula Elemental analysis Calcd. (%) Found (%) | Synthetic process |
|---|---|---|---|---|
| 1 | | 117–118 Colorless crystals | C$_{12}$H$_{10}$FN$_3$ C, 66.97; H, 4.68; N, 19.52; C, 67.09; H, 4.74; N, 19.40; | A and B |
| 2 | | 203–204 Greenish brown needles | C$_{12}$H$_{10}$FN$_3$.2/5H$_2$O C, 55.35; H, 4.58; N, 8.60; C, 55.26; H, 4.67; N, 8.45; | A |
| 3 | | 195–196 Brown needles | C$_{12}$H$_{10}$N$_4$O$_2$.1/10H$_2$O C, 59.06; H, 4.21; N, 22.96; C, 59.05; H, 4.26; N, 22.56; | A |
| 4 | | 131–132 Light-brown powder | C$_{13}$H$_{13}$N$_3$ C, 73.91; H, 6.20; N, 19.89; C, 74.10; H, 6.41; N, 19.62; | A |
| 5 | | 104–105 Light-brown powder | C$_{14}$H$_{15}$N$_3$ C, 74.64; H, 6.71; N, 18.65; C, 74.75; H, 6.89; N, 18.30; | B |

TABLE 2-continued

| Compound No. | Structural formula | m.p. (° C.) State | Molecular formula Elemental analysis Calcd. (%) Found (%) | Synthetic process |
|---|---|---|---|---|
| 6 | | 205–206 Light-brown powder | $C_{12}H_{10}ClN_3$<br>C, 62.21; H, 4.35; N, 18.14;<br>C, 62.07; H, 4.50; N, 18.00; | B |
| 7 | | 129–130 Light-yellow scales | $C_{14}H_{15}N_3$<br>C, 74.64; H, 6.71; N, 18.65;<br>C, 74.52; H, 6.66; N, 18.63; | B |
| 8 | | 228–230 Yellow powder | $C_{11}H_{10}N_4$<br>C, 66.65; H, 5.09; N, 28.26;<br>C, 66.44; H, 5.07; N, 27.95; | A |
| 9 | | 155–156 Colorless prisms | $C_{12}H_9Cl_2N_3 \cdot H_2O$<br>C, 52.39; H, 3.66; N, 15.27;<br>C, 52.50; H, 3.80; N, 14.84; | A |
| 10 | | 213–214 Yellow scales | $C_{11}H_{10}N_4$<br>C, 66.65; H, 5.09; N, 28.26;<br>C, 66.46; H, 5.14; N, 28.18; | A |
| 11 | | 203–205 Yellowish green powder | $C_{16}H_{13}N_3$<br>C, 77.71; H, 5.30; N, 16.99;<br>C, 77.46; H, 5.30; N, 16.74; | A |

TABLE 2-continued

| Compound No. | Structural formula | m.p. (° C.) State | Molecular formula Elemental analysis Calcd. (%) Found (%) | Synthetic process |
|---|---|---|---|---|
| 12 | 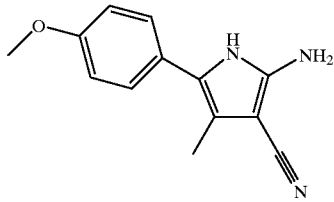 | 188–189 Light yellow needles | $C_{13}H_{13}N_3O$<br>C, 68.70; H, 5.77; N, 18.49;<br>C, 68.84; H, 5.73; N, 18.65; | A |
| 13 | 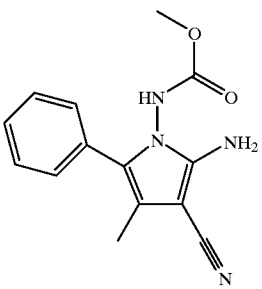 | 178–179 Colorless needles | $C_{14}H_{14}N_4O_2$<br>C, 62.21; H, 5.22; N, 20.73;<br>C, 62.25; H, 4.96; N, 20.72; | D |
| 14 | 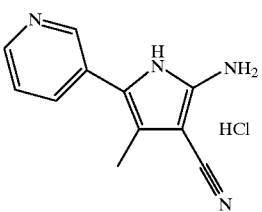 | 279–281 Reddish brown crystals | $C_{11}H_{10}N_4 \cdot HCl$<br>C, 56.30; H, 4.72; N, 23.89;<br>C, 56.08; H, 4.80; N, 23.90; | A |
| 15 | 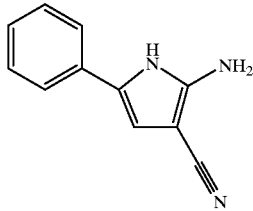 | 190–191 Light-purple crystals | $C_{11}H_9N_3$<br>C, 72.11; H, 4.95; N, 22.94;<br>C, 72.41; H, 5.12; N, 22.87; | A |
| 16 | 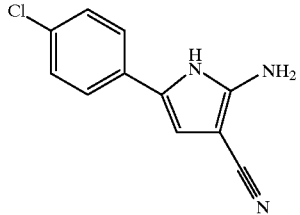 | 247–248 Gray prisms | $C_{11}H_8ClN_3$<br>C, 60.70; H, 3.70; N, 19.31;<br>C, 60.73; H, 3.85; N, 19.64; | A |
| 17 | 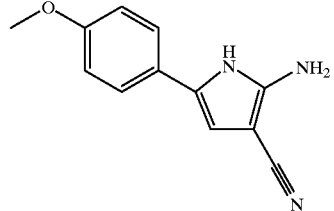 | 216–220 Light-brown crystals | $C_{12}H_{11}N_3O \cdot 1/2OH_2O$<br>C, 67.31; H, 5.22; N, 19.62;<br>C, 67.58; H, 5.14; N, 19.30; | A |

TABLE 2-continued

| Compound No. | Structural formula | m.p. (° C.) State | Molecular formula Elemental analysis Calcd. (%) Found (%) | Synthetic process |
|---|---|---|---|---|
| 18 | | 221–224 silver-colored crystals | $C_{12}H_{11}N_3$ C, 73.07; H, 5.62; N, 21.30; C, 73.00; H, 5.61; N, 21.20; | A |
| 19 | | 159–160 Grayish green crystals | $C_{12}H_{11}N_3O$ C, 67.59; H, 5.20; N, 19.71; C, 67.64; H, 5.23; N, 19.50; | A |
| 20 | | 153–155 Grayish brown crystals | $C_{12}H_{11}N_3O$ C, 67.59; H, 5.20; N, 19.71; C, 67.47; H, 5.30; N, 19.44; | A |
| 21 | | 117–118 Light-green crystals | $C_{10}H_9N_3S$ C, 59.09; H, 4.46; N, 20.67; C, 59.26; H, 4.48; N, 20.76; | A |
| 22 | | 166–167 Light-brown crystals | $C_{14}H_{15}N_3O$ C, 69.69; H, 6.27; N, 17.41; C, 69.95; H, 6.25; N, 17.51; | A |
| 23 | | 218–219 Light-brown crystals | $C_{12}H_9Cl_2N_3$ C, 54.16; H, 3.41; N, 15.79; C, 53.82; H, 3.41; N, 15.78; | A |

TABLE 2-continued

| Compound No. | Structural formula | m.p. (° C.) State | Molecular formula Elemental analysis Calcd. (%) Found (%) | Synthetic process |
|---|---|---|---|---|
| 24 | | 212–213 Pale purple crystals | $C_{12}H_{10}ClN_3$<br>C, 62.21; H, 4.35; N, 18.14;<br>C, 62.39; H, 4.43; N, 18.24; | A |
| 25 | | 206–209 Light-purple crystals | $C_{12}H_{10}BrN_3$<br>C, 52.19; H, 3.65; N, 15.22;<br>C, 52.07; H, 3.68; N, 15.17; | A |
| 26 | | 160–161 Colorless crystals | $C_{19}H_{17}N_3O$<br>C, 75.23; H, 5.65; N, 13.85;<br>C, 75.06; H, 5.75; N, 13.80; | A |
| 27 | | 113–115 Gray crystals | $C_{14}H_{15}N_3O_2$<br>C, 65.36; H, 5.88; N, 16.33;<br>C, 65.17; H, 5.92; N, 16.38; | A |
| 28 | | 216–218 Pale pink crystals | $C_{12}H_{10}BrN_3$<br>C, 52.19; H, 3.65; N, 15.22;<br>C, 52.23; H, 3.75; N, 15.28; | A |
| 29 | | 180–181 Green crystals | $C_{15}H_{18}BrN_3O_2$<br>C, 52.76; H, 4.98; N, 11.54;<br>C, 52.62; H, 5.01; N, 11.32; | A |

TABLE 2-continued

| Compound No. | Structural formula | m.p. (° C.) State | Molecular formula Elemental analysis Calcd. (%) Found (%) | Synthetic process |
|---|---|---|---|---|
| 30 | | 114–117 Light-yellow crystals | $C_{14}H_{15}N_3O$ C, 69.69; H, 6.27; N, 17.41; C, 69.86; H, 6.27; N, 17.37; | A |
| 31 | | 198–200 Gray crystals | $C_{13}H_{11}N_3O_2$ C, 64.72; H, 4.60; N, 17.42; C, 64.76; H, 4.76; N, 17.44; | A |
| 32 | | 118–119 Colorless crystals | $C_{15}H_{17}N_3O$ C, 70.56; H, 6.71; N, 16.46; C, 70.82; H, 6.77; N, 16.60; | A |
| 33 | | 234–237 Light-green crystals | $C_{13}H_{13}N_3O$ C, 68.70; H, 5.77; N, 18.49; C, 68.67; H, 5.94; N, 18.50; | A |
| 34 | | 157–158 Light-pink crystals | $C_{12}H_9Cl_2N_3$ C, 54.16; H, 3.41; N, 15.79; C, 54.34; H, 3.41; N, 15.98; | A |
| 35 | | 138–140 Light-gray crystals | $C_{13}H_{12}ClN_3$ C, 63.55; H, 4.92; N, 17.10; C, 63.58; H, 4.77; N, 17.06; | A |

TABLE 2-continued

| Compound No. | Structural formula | m.p. (° C.) State | Molecular formula Elemental analysis Calcd. (%) Found (%) | Synthetic process |
|---|---|---|---|---|
| 36 | | 158–159 Light-brown crystals | C₁₃H₁₃N₃O C, 68.70; H, 5.77; N, 18.49; C, 68.87; H, 5.89; N, 18.50; | A |
| 37 | | 177–180 Gray crystals | C₁₄H₁₅N₃O C, 69.69; H, 6.27; N, 17.41; C, 69.53; H, 6.39; N, 17.32; | A |
| 38 | | 278–281 Pale brown crystals | C₁₇H₁₃N₃ C, 78.74; H, 5.05; N, 16.20; C, 78.83; H, 5.25; N, 16.30; | A |
| 39 | | 224–226 Light-brown crystals | C₁₅H₁₁N₃ C, 77.23; H, 4.75; N, 18.01; C, 77.30; H, 4.96; N, 18.01; | A |
| 40 | | 257–260 Light-brown crystals | C₁₁H₇Cl₂N₃ C, 52.41; H, 2.80; N, 16.67; C, 52.46; H, 2.98; N, 16.45; | A |
| 41 | | 214–218 Light-purple crystals | C₁₁H₈FN₃ C, 65.67; H, 4.01; N, 20.88; C, 66.03; H, 4.24; N, 20.95; | A |

TABLE 2-continued

| Compound No. | Structural formula | m.p. (° C.) State | Molecular formula Elemental analysis Calcd. (%) Found (%) | Synthetic process |
|---|---|---|---|---|
| 42 | 3,5-bis(trifluoromethyl)phenyl-substituted 2-amino-4-methyl-3-cyanopyrrole | 230–231 Light-orange crystals | C₁₄H₉F₆N₃ C, 50.46; H, 2.72; N, 12.61; C, 50.71; H, 2.62; N, 12.56; | A |
| 43 | 2-furyl-substituted 2-amino-4-methyl-3-cyanopyrrole | 155–156 Light-red crystals | C₁₀H₉N₃O C, 64.16; H, 4.85; N, 22.45; C, 64.34; H, 5.11; N, 22.37; | A |
| 44 | 3-thienyl-substituted 2-amino-3-cyanopyrrole | 203–206 Light-purple crystals | C₉H₇N₃S C, 57.12; H, 3.73; N, 22.21; C, 57.32; H, 3.84; N, 22.19; | A |
| 45 | 4-pyridyl-substituted 2-amino-4-methyl-3-cyanopyrrole | 215–220 Yellowish brown crystals | C₁₁H₁₀N₄·1/2H₂O C, 63.75; H, 5.35; N, 27.04; C, 63.75; H, 5.31; N, 26.74; | A |
| 46 | 3-pyridyl-substituted 2-amino-3-cyanopyrrole | 241–244 Light-brown crystals | C₁₀H₈N₄ C, 65.21; H, 4.38; N, 30.42; C, 65.38; H, 4.60; N, 30.56; | A |
| 47 | 3-pyridyl-substituted 2-amino-3-cyanopyrrole HCl | ≧275 Orange-colored crystals | C₁₀H₈N₄·HCl C, 54.43; H, 4.11; N, 25.39; C, 54.31; H, 4.31; N, 25.41; | A |

Molecular formulas rendered: $C_{14}H_9F_6N_3$, $C_{10}H_9N_3O$, $C_9H_7N_3S$, $C_{11}H_{10}N_4 \cdot 1/2 H_2O$, $C_{10}H_8N_4$, $C_{10}H_8N_4 \cdot HCl$.

TABLE 2-continued

| Compound No. | Structural formula | m.p. (° C.) State | Molecular formula Elemental analysis Calcd. (%) Found (%) | Synthetic process |
|---|---|---|---|---|
| 48 | | 180–181 Gray crystals | $C_9H_7N_3S$ C, 57.12; H, 3.73; N, 22.21; C, 57.20; H, 3.78; N, 22.08; | A |
| 49 | | 192–193 Brown crystals | $C_{11}H_8ClN_3$ C, 60.70; H, 3.70; N, 19.31; C, 60.88; H, 3.67; N, 19.34; | A |
| 50 | | 235–239 Light-gray crystals | $C_{12}H_9N_3O_2$ C, 63.43; H, 3.99; N, 18.49; C, 63.52; H, 4.00; N, 18.47; | A |
| 51 | | 234–237 Purple crystals | $C_{12}H_{10}ClN_3$ C, 62.21; H, 4.35; N, 18.14; C, 62.18; H, 4.24; N, 18.17; | A |
| 52 | | 216–217 Light-brown prisms | $C_{12}H_9N_3O$ C, 68.24; H, 4.29; N, 19.89; C, 68.29; H, 4.52; N, 19.81; | A |
| 53 | | 215–217 Light-gray crystals | $C_{11}H_7F_2N_3$ C, 60.28; H, 3.22; N, 19.17; C, 60.71; H, 3.53; N, 19.31; | A |

TABLE 2-continued

| Compound No. | Structural formula | m.p. (° C.) State | Molecular formula Elemental analysis Calcd. (%) Found (%) | Synthetic process |
|---|---|---|---|---|
| 54 | 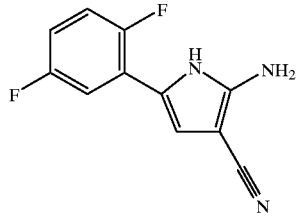 | 222–224 Gray crystals | $C_{11}H_7F_2N_3$<br>C, 60.28; H, 3.22; N, 19.17;<br>C, 60.45; H, 3.15; N, 19.22; | A |
| 55 | 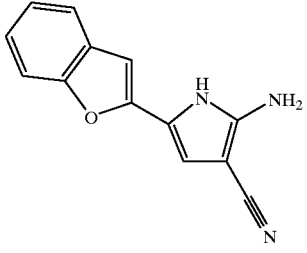 | 247–251 Pale brown crystals | $C_{13}H_9N_3O$<br>C, 69.95; H, 4.06; N, 18.82;<br>C, 70.30; H, 4.04; N, 19.02; | A |
| 56 | 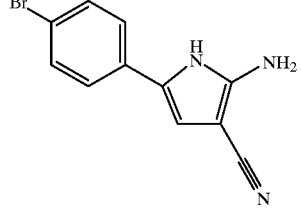 | 260–263 Purple crystals | $C_{11}H_8BrN_3$<br>C, 50.41; H, 3.08; N, 16.03;<br>C, 50.26; H, 3.04; N, 16.07; | A |
| 57 | 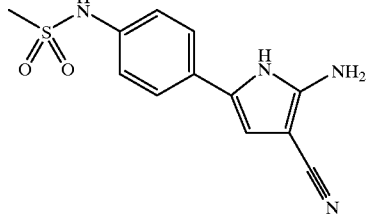 | 265–270 Light-brown crystals | $C_{12}H_{12}N_4O_2S \cdot 1/5H_2O$<br>C, 51.49; H, 4.47; N, 20.02;<br>C, 51.67; H, 4.44; N, 19.67; | A |
| 58 | 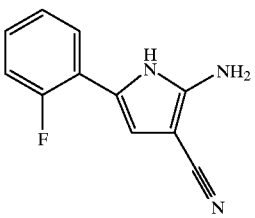 | 189–191 Light-yellow plates | $C_{11}H_8FN_3$<br>C, 65.67; H, 4.01; N, 20.88;<br>C, 66.15; H, 4.14; N, 20.81; | A |
| 59 | 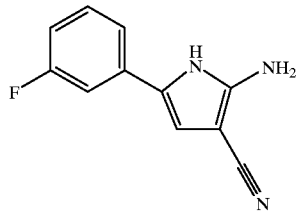 | 192–193 Gray crystals | $C_{11}H_8FN_3 \cdot 1/25C_6H_6$<br>C, 66.07; H, 4.06; N, 20.57;<br>C, 66.38; H, 4.23; N, 21.01; | A |

TABLE 2-continued

| Compound No. | Structural formula | m.p. (° C.) State | Molecular formula Elemental analysis Calcd. (%) Found (%) | Synthetic process |
|---|---|---|---|---|
| 60 | | 183–184 Light-brown needles | $C_{12}H_8F_3N_3$<br>C, 57.37; H, 3.21; N, 16.73;<br>C, 57.40; H, 3.14; N, 16.86; | A |
| 61 | | 160–161 Colorless prisms | $C_1H_{10}ClN_3$<br>C, 62.21; H, 4.35; N, 18.14;<br>C, 62.29; H, 4.38; N, 18.55; | A |
| 62 | | 108–109 Colorless needles | $C_{13}H_{13}N_3O.1/5H_2O$<br>C, 67.63; H, 5.85; N, 18.20;<br>C, 67.79; H, 5.79; N, 18.22; | A |
| 63 | | 146–147 Yellow powder | $C_{12}H_9F_2N_3$<br>C, 61.80; H, 3.89; N, 18.02;<br>C, 61.71; H, 3.91; N, 17.69; | A |
| 64 | | 127–128 Pale pink needles | $C_{13}H_{13}N_3$<br>C, 73.91; H, 6.20; N, 19.89;<br>C, 73.84; H, 6.28; N, 19.76; | A |
| 65 | | 181–182 Yellow powder | $C_{12}H_9F_2N_3$<br>C, 61.80; H, 3.89; N, 18.02;<br>C, 61.93; H, 3.98; N, 18.09; | A |

TABLE 2-continued

| Compound No. | Structural formula | m.p. (° C.) State | Molecular formula Elemental analysis Calcd. (%) Found (%) | Synthetic process |
|---|---|---|---|---|
| 66 | | 177–178 Light-brown needles | $C_{13}H_{10}F_3N_3$<br>C, 58.87; H, 3.80; N, 15.84;<br>C, 58.88; H, 3.88; N, 15.96; | A |
| 67 | | 202–203 Colorless needles | $C_{13}H_{10}F_3N_3$<br>C, 58.87; H, 3.80; N, 15.84;<br>C, 58.58; H, 3.82; N, 15.73; | A |
| 68 | | 223–225 Greenish brown needles | $C_{14}H_{13}N_3O_2$<br>C, 65.87; H, 5.13; N, 16.46;<br>C, 65.76; H, 5.19; N, 16.30; | A |
| 69 | | 143–144 Colorless crystals | $C_{13}H_{12}FN_3O$<br>C, 63.67; H, 4.93; N, 17.13;<br>C, 63.66; H, 4.92; N, 16.84; | A |
| 70 | | 270–272 Yellow crystals | $C_{17}H_{19}N_3$<br>C, 76.95; H, 7.22; N, 15.84;<br>C, 76.87; H, 7.22; N, 15.95; | A |
| 71 | | 253–260 Light-blue crystals | $C_{16}H_{17}N_3$<br>C, 76.46; H, 6.82; N, 16.72;<br>C, 76.41; H, 6.61; N, 16.71; | A |

TABLE 2-continued

| Compound No. | Structural formula | m.p. (° C.) State | Molecular formula Elemental analysis Calcd. (%) Found (%) | Synthetic process |
|---|---|---|---|---|
| 72 | | 245–247 Colorless crystals | C₁₆H₁₆FN₃O C, 67.35; H, 5.65; N, 14.73; C, 67.14; H, 5.86; N, 14.69; | A |
| 73 | | 140–141 Light-yellow needles | C₁₆H₁₅N₃O C, 72.43; H, 5.70; N, 15.84; C, 72.42; H, 5.64; N, 15.79; | G |
| 74 | | 151–152 Light-yellow powder | C₁₉H₁₆FN₃ C, 74.74; H, 5.28; N, 13.76; C, 74.78; H, 5.38; N, 13.50; | F |
| 75 | | 138–139 Light-yellow needles | C₁₃H₁₃N₃ C, 73.91; H, 6.20; N, 19.89; C, 73.85; H, 6.72; N, 19.66; | F |
| 76 | | 195–197 Colorless crystals | C₁₂H₁₃N₃O C, 66.96; H, 6.09; N, 19.52; C, 66.95; H, 6.23; N, 19.38; | A |
| 77 | | 247–248 Light-brown needles | C₁₂H₉N₃O₂ C, 63.43; H, 3.99; N, 18.49; C, 63.44; H, 3.89; N, 18.53; | H |

TABLE 2-continued

| Compound No. | Structural formula | m.p. (° C.) State | Molecular formula Elemental analysis Calcd. (%) Found (%) | Synthetic process |
|---|---|---|---|---|
| 78 | | 235–236 Orange-colored needles | C₁₂H₉N₃O₂ C, 63.43; H, 3.99; N, 18.49; C, 63.35; H, 3.96; N, 18.56; | H |
| 79 | | 239–240 Yellow powder | C₁₇H₁₁N₃O₂ C, 70.58; H, 3.83; N, 14.53; C, 70.70; H, 3.93; N, 14.50; | H |
| 80 | | 220–221 Light-yellow needles | C₁₂H₉N₃O₂ C, 63.43; H, 3.99; N, 18.49; C, 63.46; H, 4.19; N, 18.17; | H |
| 81 | | 260–262 Light-yellow powder | C₁₂H₉N₃O₂ C, 63.43; H, 3.99; N, 18.49; C, 63.27; H. 3.98; N, 18.26; | H |
| 82 | | 163–164 Colorless prisms | C₁₂H₁₁N₃ C, 73.07; H, 5.62; N, 21.30; C, 73.47; H, 5.61; N, 21.38; | I |
| 83 | | 189–190 Colorless scales | C₁₂H₉ClN₂ C, 66.52; H, 4.19; N, 12.93; C, 66.51; H, 4.24; N, 12.86; | H |

TABLE 2-continued

| Compound No. | Structural formula | m.p. (° C.) State | Molecular formula Elemental analysis Calcd. (%) Found (%) | Synthetic process |
|---|---|---|---|---|
| 84 | 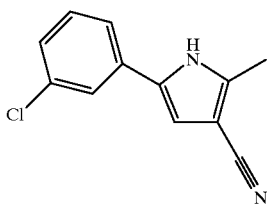 | 208–209 Light-brown powder | $C_{12}H_9ClN_2$<br>C, 66.52; H, 4.19; N, 12.93;<br>C, 66.47; H, 4.21; N, 12.87; | H |
| 85 | 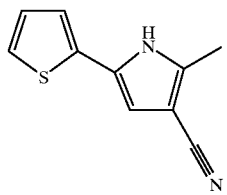 | 160–161 Colorless powder | $C_{10}H_8N_2S.1/5H_2O$<br>C, 62.60; H, 4.31; N, 14.60;<br>C, 62.63; H, 4.31; N, 14.64; | H |
| 86 | 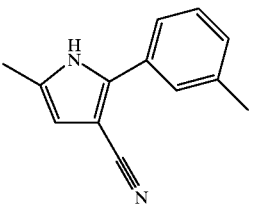 | 185–186 Colorless powder | $C_{13}H_{12}N_2$<br>C, 79.56; H, 6.16; N, 14.27;<br>C, 79.45; H, 5.94; N, 14.34; | H |
| 87 | 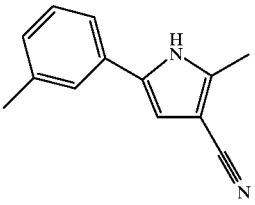 | 170–173 Colorless powder | $C_{13}H_{12}N_2$<br>C, 79.56; H, 6.16; N, 14.27;<br>C, 79.31; H, 6.19; N, 14.33; | H |
| 88 | 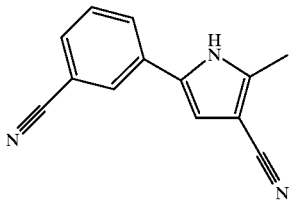 | 252–253 Colorless powder | $C_{13}H_9N_3$<br>C, 75.35; H, 4.38; N, 20.28;<br>C, 75.27; H, 4.39; N, 20.13; | H |
| 89 | 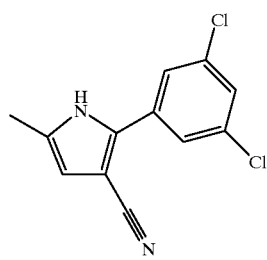 | 270–271 Colorless powder | $C_{12}H_8Cl_2N_2$<br>C, 57.40; H, 3.21; N, 11.16;<br>C, 57.15; H, 3.34; N, 11.05; | H |

TABLE 2-continued

| Compound No. | Structural formula | m.p. (° C.) State | Molecular formula Elemental analysis Calcd. (%) Found (%) | Synthetic process |
|---|---|---|---|---|
| 90 | | 275–276 Colorless needles | $C_{12}H_8Cl_2N_2$ C, 57.40; H, 3.21; N, 11.16; C, 57.36; H, 3.34; N, 11.24; | H |
| 91 | | 213–214 Colorless powder | $C_{12}H_9FN_2 \cdot 1/4H_2O$ C, 70.40; H, 4.67; N, 13.68; C, 70.60; H, 4.81; N, 13.88; | H |
| 92 | | 117–118 Colorless powder | $C_{14}H_{14}N_2$ C, 79.97; H, 6.71; N, 13.32; C, 80.13; H, 7.00; N, 13.32; | H |
| 93 | | 176–177 Colorless powder | $C_{14}H_{14}N_2$ C, 79.97; H, 6.71; N, 13.32; C, 80.14; H, 6.65; N, 13.32; | H |
| 94 | | 167–168 Colorless powder | $C_{13}H_{11}ClN_2$ C, 67.68; H, 4.81; N, 12.14; C, 67.56; H, 4.81; N, 12.12; | H |
| 95 | | 138–139 Colorless powder | $C_{13}H_{11}ClN_2 \cdot 1/5H_2O$ C, 66.64; H, 4.90; N, 11.96; C, 66.45; H, 4.72; N, 11.87; | H |

TABLE 2-continued

| Compound No. | Structural formula | m.p. (° C.) State | Molecular formula Elemental analysis Calcd. (%) Found (%) | Synthetic process |
|---|---|---|---|---|
| 96 | | 172–173 Colorless powder | $C_{14}H_{13}ClN_2$ C, 68.71; H, 5.35; N, 11.45; C, 68.68; H, 5.62; N, 11.70; | H |
| 97 | | 105–106 Colorless powder | $C_{14}H_{13}ClN_2$ C, 68.71; H, 5.25; N, 11.45; C, 68.71; H, 5.54; N, 11.61; | H |
| 98 | | 91–92 Colorless powder | $C_{15}H_{15}ClN_2 \cdot 1/10H_2O$ C, 69.15; H, 5.88; N, 10.75; C, 68.96; H, 6.09; N, 10.68; | H |
| 99 | | 167–168 Light-yellow powder | $C_{23}H_{25}N_3O$ C, 76.85; H, 7.01; N, 11.69; C, 76.60; H, 7.18; N, 11.68; | F |
| 100 | | 180–182 Light-yellow scales | $C_{19}H_{17}N_3$ C, 79.41; H, 5.96; N, 14.62; C, 80.00; H, 6.05; N, 14.43; | F |
| 101 | | 144–146 Colorless needles | $C_{17}H_{15}N_3O$ C, 73.63; H, 5.45; N, 15.15; C, 73.37; H, 5.39; N, 14.92; | F |

TABLE 2-continued

| Compound No. | Structural formula | m.p. (° C.) State | Molecular formula Elemental analysis Calcd. (%) Found (%) | Synthetic process |
|---|---|---|---|---|
| 102 | | 235–237 Colorless crystals | $C_{16}H_{17}N_3$ C, 76.46; H, 6.82; N, 16.72; C, 76.37; H, 6.82; N, 16.54; | A |
| 103 | | 218–219 Colorless crystals | $C_{16}H_{17}N_3O$ C, 71.89; H, 6.41; N, 15.72; C, 71.68; H, 6.12; N, 15.73; | A |
| 104 | | 233–236 Light-yellow crystals | $C_{16}H_{17}N_3O$ C, 71.89; H, 6.41; N, 15.72; C, 71.88; H, 6.40; N, 15.59; | A |
| 105 | | 264–265 Light-blue crystals | $C_{15}H_{14}ClN_3 \cdot 1/10H_2O$ C, 65.86; H, 5.23; N, 15.26; C, 65.62; H, 4.89; N, 15.26; | A |
| 106 | | 191–192 Light-brown crystals | $C_{17}H_{19}N_3O$ C, 72.57; H, 6.81; N, 14.94; C, 72.71; H, 6.96; N, 15.09; | A |
| 107 | | 256–258 Colorless crystals | $C_{16}H_{16}ClN_3$ C, 67.25; H, 5.64; N, 14.70; C, 67.14; H, 5.64; N, 14.78; | A |

TABLE 2-continued

| Compound No. | Structural formula | m.p. (° C.) State | Molecular formula Elemental analysis Calcd. (%) Found (%) | Synthetic process |
|---|---|---|---|---|
| 108 | (4-chlorophenyl)-pyrrole-morpholine with CN | 260–262 Blue crystals | $C_{15}H_{14}ClN_3O$ C, 62.61; H, 4.90; N, 14.60; C, 62.33; H, 5.05; N, 14.71; | A |
| 109 | (4-methoxyphenyl)-pyrrole-morpholine with CN | 226–228 Light-blue crystals | $C_{16}H_{17}N_3O_2$ C, 67.83; H, 6.05; N, 14.83; C, 67.79; H, 6.15; N, 14.66; | A |
| 110 | (4-methylphenyl)-pyrrole-morpholine with CN | 227–228 Light-yellow crystals | $C_{17}H_{19}N_3O$ C, 72.57; H, 6.81; N, 14.94; C, 72.39; H, 6.87; N, 14.86; | A |
| 111 | (4-methylphenyl)-methylpyrrole-piperidine with CN | 225–228 Light-yellow crystals | $C_{18}H_{21}N_3$ C, 77.38; H, 7.58; N, 15.04; C, 77.08; H, 7.50; N, 15.03; | A |
| 112 | (4-bromophenyl)-pyrrole-morpholine with CN | 271–273 Blue needles | $C_{15}H_{14}BrN_3O$ C, 54.23; H, 4.25; N, 12.65; C, 54.22; H, 4.45; N, 12.62; | A |
| 113 | (4-nitrophenyl)-pyrrole-piperidine with CN | 281–283 Reddish brown needles | $C_{16}H_{16}N_4O_2$ C, 64.85; H, 5.44; N, 18.91; C, 64.74; H, 5.52; N, 18.82; | A |

TABLE 2-continued

| Compound No. | Structural formula | m.p. (° C.) State | Molecular formula Elemental analysis Calcd. (%) Found (%) | Synthetic process |
|---|---|---|---|---|
| 114 | | 239–240 Blue plates | $C_{17}H_{19}N_3$ C, 76.95; H, 7.22; N, 15.84; C, 76.91; H, 7.05; N, 15.82; | A |
| 115 | | 219–220 Light-blue crystals | $C_{16}H_{17}N_3O$ C, 71.89; H, 6.41; N, 15.72; C, 71.81; H, 6.73; N, 15.70; | A |
| 116 | | ≧300 Reddish brown needles | $C_{15}H_{14}N_4O_3$ C, 60.40; H, 4.73; N, 18.78; C, 60.30; H, 5.01; N, 18.63; | A |
| 117 | | 233–236 Light-pink needles | $C_{17}H_{19}N_3O$ C, 72.57; H, 6.81; N, 14.94; C, 72.55; H, 6.45; N, 14.88; | A |
| 118 | | 194–195 Light-brown crystals | $C_{18}H_{21}N_3O$ C, 73.19; H, 7.17; N, 14.23; C, 73.20; H, 7.49; N, 14.22; | A |
| 119 | | 200–202 Light-brown crystals | $C_{17}H_{19}N_3O_2$ C, 68.67; H, 6.44; N, 14.13; C, 68.49; H, 6.55; N, 14.05; | A |

TABLE 2-continued

| Compound No. | Structural formula | m.p. (° C.) State | Molecular formula Elemental analysis Calcd. (%) Found (%) | Synthetic process |
|---|---|---|---|---|
| 120 | | 163–164 Light-brown crystals | C₁₆H₁₉N₃ C, 75.85; H, 7.56; N, 16.59; C, 75.60; H, 7.86; N, 16.48; | A |
| 121 | | 181–182 Colorless crystals | C₁₇H₁₈FN₃ C, 72.06; H, 6.40; N, 14.83; C, 72.03; H, 6.62; N, 14.85; | A |
| 122 | | 112–114 Colorless powder | C₁₆H₁₈FN₃ C, 70.83; H, 6.69; N, 15.49; C, 71.30; H, 6.46; N, 15.51; | A |
| 123 | | 245–250 Colorless crystals | C₁₆H₁₆FN₃ C, 71.36; H, 5.99; N, 15.60; C, 71.32; H, 6.01; N, 15.64; | A |
| 124 | | 145–146 Colorless crystals | C₁₆H₁₈FN₃ C, 70.83; H, 6.69; N, 15.49; C, 70.81; H, 6.50; N, 15.62; | A |
| 125 | | 228–229 Colorless crystals | C₁₇H₁₈FN₃ C, 72.06; H, 6.40; N, 14.83; C, 72.27; H, 6.48; N, 14.43; | A |

TABLE 2-continued

| Compound No. | Structural formula | m.p. (° C.) State | Molecular formula Elemental analysis Calcd. (%) Found (%) | Synthetic process |
|---|---|---|---|---|
| 126 | | 215–217 Light-brown crystals | $C_{14}H_{15}N_3S$ C, 65.34; H, 5.88; N, 16.33; C, 65.48; H, 6.14; N, 16.26; | A |
| 127 | | 260–265 Colorless crystals | $C_{16}H_{15}Cl_2N_3$ C, 60.01; H, 4.72; N, 13.12; C, 60.17; H, 4.93; N, 13.09; | A |
| 128 | | 207–209 Colorless crystals | $C_{17}H_{17}Cl_2N_3$ C, 61.09; H, 5.13; N, 12.57; C, 61.06; H, 5.31; N, 12.53; | A |
| 129 | | 220–226 Colorless crystals | $C_{18}H_{21}N_3O$ C, 73.19; H, 7.17; N, 14.23; C, 73.00; H, 7.29; N, 14.41; | A |
| 130 | | 207–212 Colorless crystals | $C_{19}H_{23}N_3O$ C, 73.76; H, 7.49; N, 13.58; C, 73.70; H, 7.58; N, 13.52; | A |
| 131 | | 270–272 Colorless crystals | $C_{16}H_{16}ClN_3$ C, 67.25; H, 5.64; N, 14.70; C, 67.27; H, 5.70; N, 14.61; | A |

TABLE 2-continued

| Compound No. | Structural formula | m.p. (° C.) State | Molecular formula Elemental analysis Calcd. (%) Found (%) | Synthetic process |
|---|---|---|---|---|
| 132 | | 250–252 Colorless crystals | $C_{17}H_{17}ClN_3$ C, 68.11; H, 6.02; N, 14.02; C, 68.13; H, 6.22; N, 13.78; | A |
| 133 | | 243–245 Colorless crystals | $C_{16}H_{16}BrN_3$ C, 58.19; H, 4.88; N, 12.72; C, 58.05; H, 4.94; N, 12.89; | A |
| 134 | | 249–253 Colorless crystals | $C_{17}H_{18}BrN_3$ C, 59.31; H, 5.27; N, 12.21; C, 59.21; H, 5.37; N, 12.28; | A |
| 135 | | 168–170 Colorless crystals | $C_{18}H_{21}N_3O_2$ C, 69.43; H, 6.80; N, 13.49; C, 69.42; H, 6.89; N, 13.63; | A |
| 136 | | 176–178 Colorless crystals | $C_{19}H_{23}N_3O_2$ C, 70.13; H, 7.12; N, 12.91; C, 70.07; H, 7.32; N, 12.93; | A |
| 137 | | 231–233 Light-yellow crystals | $C_{16}H_{16}ClN_3$ C, 67.25; H, 5.64; N, 14.70; C, 67.41; H, 5.54; N, 14.83; | A |

TABLE 2-continued

| Compound No. | Structural formula | m.p. (° C.) State | Molecular formula Elemental analysis Calcd. (%) Found (%) | Synthetic process |
|---|---|---|---|---|
| 138 | | 246–248 Light-brown crystals | $C_{16}H_{16}BrN_3$ C, 58.19; H, 4.88; N, 12.72; C, 58.08; H, 4.96; N, 12.76; | A |
| 139 | | 219–220 Light-gray crystals | $C_{17}H_{19}N_3O$ C, 72.57; H, 6.81; N, 14.94; C, 72.50; H, 6.86; N, 14.84; | A |
| 140 | | 171–172 Colorless crystals | $C_{18}H_{21}N_3O$ C, 73.19; H, 7.17; N, 14.23; C, 73.15; H, 7.00; N, 14.23; | A |
| 141 | | 229–235 Light-brown crystals | $C_{19}H_{23}N_3O$ C, 73.76; H, 7.49; N, 13.58; C, 73.55; H, 7.54; N, 13.45; | A |
| 142 | | 242–246 Colorless crystals | $C_{20}H_{25}N_3O$ C, 74.27; H, 7.79; N, 12.99; C, 74.09; H, 7.52; N, 12.96; | A |
| 143 | | 245–252 Light-brown crystals | $C_{17}H_{17}N_3O_2$ C, 69.14; H, 5.80; N, 14.23; C, 69.24; H, 5.83; N, 14.36; | A |

TABLE 2-continued

| Compound No. | Structural formula | m.p. (° C.) State | Molecular formula Elemental analysis Calcd. (%) Found (%) | Synthetic process |
|---|---|---|---|---|
| 144 | | 192–195 Light-blue crystals | $C_{18}H_{19}N_3O_2$ C, 69.88; H, 6.19; N, 13.58; C, 69.81; H, 6.17; N, 13.71; | A |
| 145 | | 246–247 Light-brown crystals | $C_{16}H_{15}Cl_2N_3$ C, 60.01; H, 4.72; N, 13.12; C, 60.03; H, 4.70; N, 13.13; | A |
| 146 | | 167–168 Light-gray needles | $C_{13}H_{12}N_2O$ C, 73.56; H, 5.70; N, 13.20; C, 73.69; H, 5.65; N, 13.14; | I |
| 147 | | 215–217 Light-brown crystals | $C_{17}H_{17}Cl_2N_3$ C, 61.09; H, 5.13; N, 12.57; C, 61.01; H, 5.19; N, 12.54; | A |
| 148 | | 224–229 Light-brown crystals | $C_{13}H_{13}N_3S$ C, 64.17; H, 5.39; N, 17.27; C, 64.16; H, 5.29; N, 17.31; | A |
| 149 | | 205–207 Light-green crystals | $C_{14}H_{15}N_3S$ C, 65.34; H, 5.88; N, 16.33; C, 65.23; H, 5.93; N, 16.11; | A |

TABLE 2-continued

| Compound No. | Structural formula | m.p. (° C.) State | Molecular formula Elemental analysis Calcd. (%) Found (%) | Synthetic process |
|---|---|---|---|---|
| 150 | | 190–192 Light-brown powder | $C_{13}H_{11}ClN_2$ C, 67.68; H, 4.81; N, 12.14; C, 67.78; H, 4.93; N, 12.21; | I |
| 151 | | 184–185 Ocherous needles | $C_{12}H_{11}N_3$ C, 73.07; H, 5.62; N, 21.30; C, 73.39; H, 5.52; N, 21.24; | I |
| 152 | | 243–249 Light-brown crystals | $C_{17}H_{18}ClN_3$ C, 68.11; H, 6.05; N, 14.02; C, 68.25; H, 6.14; N, 13.96; | A |
| 153 | | 187–188 Colorless needles | $C_{14}H_{13}ClN_2$ C, 68.71; H, 5.35; N, 11.45; C, 68.77; H, 5.46; N, 11.40; | I |
| 154 | | 206–207 Colorless crystals | $C_{18}H_{20}ClN_3$ C, 68.89; H, 6.42; N, 13.39; C, 68.78; H, 6.55; N, 13.41; | A |
| 155 | | 210–213 Light-brown crystals | $C_{17}H_{19}N_3O$ C, 72.57; H, 6.81; N, 14.94; C, 72.39; H, 6.92; N, 14.83; | A |

TABLE 2-continued

| Compound No. | Structural formula | m.p. (° C.) State | Molecular formula Elemental analysis Calcd. (%) Found (%) | Synthetic process |
|---|---|---|---|---|
| 156 | 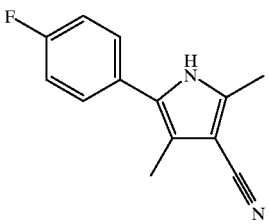 | 199–201 Light-red needles | $C_{13}H_{11}FN_2$<br>C, 72.88; H, 5.18; N, 13.08;<br>C, 73.15; H, 5.04; N, 13.13; | I |
| 157 | 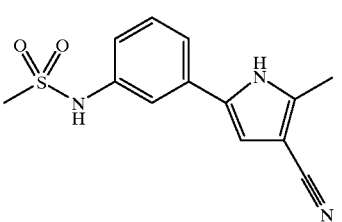 | 221–222 Light-yellow crystals | $C_{13}H_{13}N_3O_2 \cdot 1/10H_2O$<br>C, 56.34; H, 4.80; N, 15.16;<br>C, 56.23; H, 4.62; N, 15.02; | I |
| 158 | 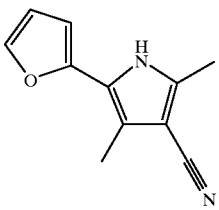 | 140–142 Light-yellow needles | $C_{11}H_{10}N_2O$<br>C, 70.95; H, 5.41; N, 15.04;<br>C, 71.07; H, 5.70; N, 15.11; | I |
| 159 | 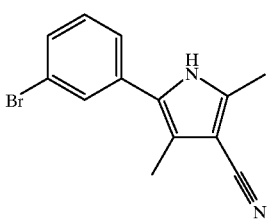 | 195–196 Colorless needles | $C_{13}H_{11}BrN_2$<br>C, 56.75; H, 4.03; N, 10.18;<br>C, 56.54; H, 4.06; N, 10.14; | I |
| 160 | 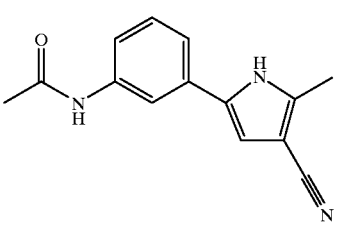 | 221–222 Light-yellow needles | $C_{14}H_{13}N_3O \cdot 1/5H_2O$<br>C, 69.23; H, 5.56; N, 17.30;<br>C, 69.26; H, 5.58; N, 17.19; | I |
| 161 | 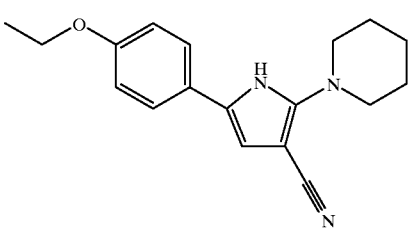 | 211–213 Light-brown crystals | $C_{18}H_{21}N_3O$<br>C, 73.19; H, 7.17; N, 14.23;<br>C, 73.07; H, 7.37; N, 14.16; | A |

TABLE 2-continued

| Compound No. | Structural formula | m.p. (° C.) State | Molecular formula Elemental analysis Calcd. (%) Found (%) | Synthetic process |
|---|---|---|---|---|
| 162 | | 203–204 Gray powder | $C_{16}H_{12}N_2$ C, 82.73; H, 5.21; N, 12.06; C, 82.91; H, 5.40; N, 12.03; | I |
| 163 | | 200–202 Light-brown crystals | $C_{18}H_{21}N_3O$ C, 73.19; H, 7.17; N, 14.23; C, 73.07; H, 7.33; N, 13.99; | A |
| 164 | | 219–223 Light-brown crystals | $C_{19}H_{23}N_3O \cdot 1/10H_2O$ C, 73.33; H, 7.77; N, 13.50; C, 73.17; H, 7.57; N, 13.28; | A |
| 165 | | 297–301 Light-yellow powder | $C_{17}H_{19}N_3O$ C, 72.57; H, 6.81; N, 14.94; C, 72.17; H, 6.45; N, 14.92; | A |
| 166 | | 140–141 Light-blue crystals | $C_{18}H_{21}N_3O \cdot 1/10H_2O$ C, 72.75; H, 7.19; N, 14.14; C, 72.60; H, 7.18; N, 14.06; | A |
| 167 | | 258–261 Light-yellow crystals | $C_{19}H_{17}N_3 \cdot 1/10H_2O$ C, 78.92; H, 6.00; N, 14.53; C, 78.81; H, 6.23; N, 14.67; | A |

TABLE 2-continued

| Compound No. | Structural formula | m.p. (° C.) State | Molecular formula Elemental analysis Calcd. (%) Found (%) | Synthetic process |
|---|---|---|---|---|
| 168 | | 240–243 Brown crystals | C₂₀H₁₉N₃·1/10H₂O C, 79.23; H, 6.38; N, 13.86; C, 79.08; H, 6.59; N, 13.71; | A |
| 169 | | 227–231 Brown crystals | C₂₁H₁₉N₃ C, 80.48; H, 6.11; N, 13.41; C, 80.23; H, 6.17; N, 13.45; | A |
| 170 | | 257–260 Light-yellow crystals | C₁₅H₁₃Cl₂N₃ C, 58.84; H, 4.28; N, 13.72; C, 58.51; H, 4.25; N, 13.83; | A |
| 171 | | 216–221 Light-brown crystals | C₁₇H₁₇N₃O₂ C, 69.14; H, 5.80; N, 14.23; C, 69.27; H, 5.68; N, 14.27; | A |
| 172 | | 231–236 Light-brown crystals | C₁₅H₁₄FN₃ C, 70.57; H, 5.53; N, 16.46; C, 70.56; H, 5.72; N, 16.63; | A |
| 173 | | 203–204 Colorless crystals | C₁₆H₁₆FN₃ C, 71.36; H, 5.99; N, 15.60; C, 71.43; H, 6.17; N, 15.64; | A |

TABLE 2-continued

| Compound No. | Structural formula | m.p. (° C.) State | Molecular formula Elemental analysis Calcd. (%) Found (%) | Synthetic process |
|---|---|---|---|---|
| 174 | | 238–240 Gray powder | C₁₃H₁₁ClN₂ C, 67.68; H, 4.81; N, 12.14; C, 68.03; H, 4.84; N, 12.22; | I |
| 175 | | 213–215 Gray powder | C₁₂H₈F₂N₂ C, 66.05; H, 3.70; N, 12.84; C, 66.13; H, 3.65; N, 12.92; | I |
| 176 | | 235–236 Light-gray crystals | C₁₅H₁₆N₄ C, 71.40; H, 6.39; N, 22.21; C, 71.35; H, 6.43; N, 22.03; | A |
| 177 | | 240–242 Brown powder | C₁₅H₁₆N₄ C, 71.40; H, 6.39; N, 22.21; C, 71.43; H, 6.49; N, 22.71; | A |
| 178 | | 251–260 Light-brown powder | C₁₄H₁₄N₄ C, 70.57; H, 5.92; N, 23.51; C, 70.19; H, 5.99; N, 23.11; | A |
| 179 | | 248–251 Light-purple crystals | C₁₄H₁₄N₄ C, 70.57; H, 5.92; N, 23.51; C, 70.58; H, 5.96; N, 23.52; | A |

TABLE 2-continued

| Compound No. | Structural formula | m.p. (° C.) State | Molecular formula Elemental analysis Calcd. (%) Found (%) | Synthetic process |
|---|---|---|---|---|
| 180 | | 270–276 Orange-colored needles | C₁₄H₁₄N₄·HCl C, 61.20; H, 5.50; N, 20.39; C, 61.23; H, 5.60; N, 20.02; | A |
| 181 | | 230–234 Brown crystals | C₁₃H₁₃N₃S.1/7H₂O C, 63.50; H, 5.45; N, 17.08; C, 63.91; H, 5.51; N, 16.68; | A |
| 182 | | 220–223 Brown crystals | C₁₅H₁₄ClN₃.1/5H₂O C, 65.43; H, 5.27; N, 15.26; C, 65.81; H, 5.15; N, 14.94; | A |
| 183 | | 236–240 Light-brown crystals | C₁₆H₁₆ClN₃ C, 67.25; H, 5.64; N, 14.70; C, 67.11; H, 5.69; N, 14.48; | A |
| 184 | | 225–228 Light-brown crystals | C₁₆H₁₅N₃O₂ C, 68.31; H, 5.37; N, 14.94; C, 68.12; H, 5.40; N, 14.81; | A |
| 185 | | 211–212 Gray powder | C₁₃H₁₀N₂O₂ C, 69.02; H, 4.46; N, 12.38; C, 69.08; H, 4.55; N, 12.37; | I |

TABLE 2-continued

| Compound No. | Structural formula | m.p. (° C.) State | Molecular formula Elemental analysis Calcd. (%) Found (%) | Synthetic process |
|---|---|---|---|---|
| 186 | 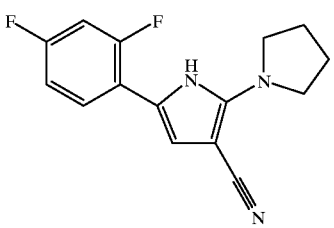 | 212–213 Colorless crystals | $C_{15}H_{13}F_2N_3$<br>C, 65.93; H, 4.79; N, 15.38;<br>C, 65.93; H, 4.68; N, 15.16; | A |
| 187 | 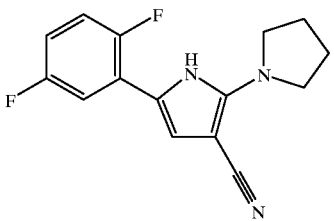 | 206–207 Light-green crystals | $C_{15}H_{13}F_2N_3$<br>C, 65.93; H, 4.79; N, 15.38;<br>C, 66.50; H, 4.92; N, 15.32; | A |
| 188 | 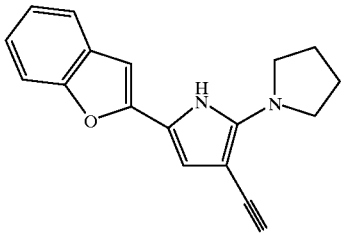 | 260–268 Light-yellow needles | $C_{17}H_{15}N_3O$<br>C, 73.68; H, 5.45; N, 15.15;<br>C, 73.68; H, 5.58; N, 15.14; | A |
| 189 | 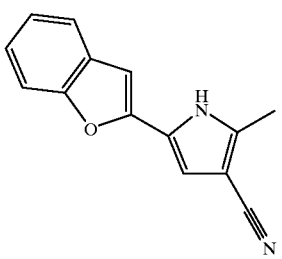 | 208–209 Light-yellow needles | $C_{14}H_{10}N_2O$<br>C, 75.66; H, 4.54; N, 12.60;<br>C, 75.50; H, 4.78; N, 12.58; | I |
| 190 | 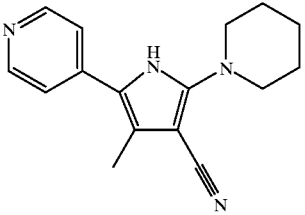 | 201–203 Reddish brown powder | $C_{16}H_{18}N_4$<br>C, 72.15; H, 6.81; N, 21.04;<br>C, 71.83; H, 6.98; N, 21.07; | A |
| 191 | 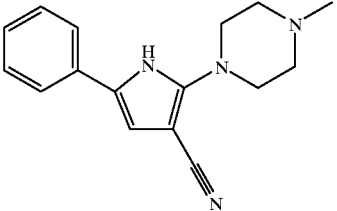 | 160–161 Light-yellow crystals | $C_{16}H_{18}N_4$<br>C, 72.15; H, 6.81; N, 21.04;<br>C, 72.11; H, 6.95; N, 20.93; | A |

TABLE 2-continued

| Compound No. | Structural formula | m.p. (° C.) State | Molecular formula Elemental analysis Calcd. (%) Found (%) | Synthetic process |
|---|---|---|---|---|
| 192 | 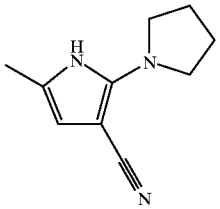 | 190–191 Purple crystals | $C_{10}H_{13}N_3$<br>C, 68.54; H, 7.48; N, 23.98;<br>C, 68.55; H, 7.35; N, 24.09; | A |
| 193 | 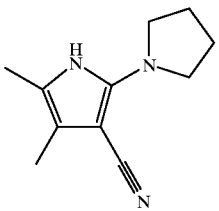 | 189–191 Purple crystals | $C_{11}H_{15}N_3$<br>C, 69.81; H, 7.99; N, 22.20;<br>C, 69.96; H, 8.16; N, 21.92; | A |
| 194 | 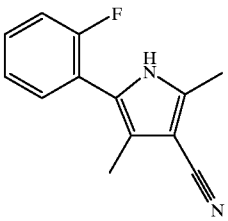 | 125–127 Colorless needles | $C_{13}H_{11}FN_2$<br>C, 72.88; H, 5.18; N, 13.08;<br>C, 73.11; H, 5.39; N, 13.08; | I |
| 195 | 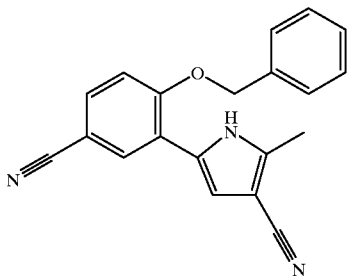 | 202–203 Colorless powder | $C_{20}H_{15}N_3O$<br>C, 76.66; H, 4.83; N, 13.41;<br>C, 76.94; H, 4.94; N, 13.37; | I |
| 196 | 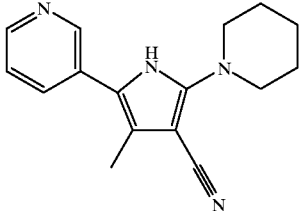 | 196–198 Light-brown crystals | $C_{16}H_{18}N_4$<br>C, 72.15; H, 6.81; N, 21.04;<br>C, 72.03; H, 6.88; N, 21.39; | A |
| 197 | 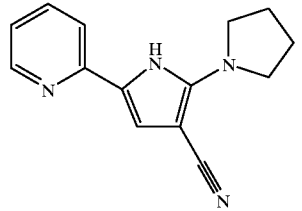 | 156–158 Light-yellow crystals | $C_{14}H_{14}N_4$<br>C, 70.57; H, 5.92; N, 23.51;<br>C, 70.72; H, 6.04; N, 23.58; | A |

TABLE 2-continued

| Compound No. | Structural formula | m.p. (° C.) State | Molecular formula Elemental analysis Calcd. (%) Found (%) | Synthetic process |
|---|---|---|---|---|
| 198 | | 164–165 Purple crystals | $C_{12}H_{17}N_3$<br>C, 70.90; H, 8.43; N, 20.67;<br>C, 70.56; H, 8.56; N, 20.67; | A |
| 199 | | 189–191 Light-brown crystals | $C_{18}H_{21}N_3O$<br>C, 73.19; H, 7.17; N, 14.23;<br>C, 73.13; H, 7.42; N, 14.27; | A |
| 200 | | 204–206 Light-blue crystals | $C_{19}H_{23}N_3O$<br>C, 73.76; H, 7.49; N, 13.58;<br>C, 73.72; H, 7.73; N, 13.63; | A |
| 201 | | 179–183 Light-green crystals | $C_{18}H_{21}N_3O_2$<br>C, 69.43; H, 6.80; N, 13.49;<br>C, 69.48; H, 6.73; N, 13.56; | A |
| 202 | | 179–180 Colorless crystals | $C_{19}H_{23}N_3O_2$<br>C, 70.13; H, 7.12; N, 12.91;<br>C, 70.01; H, 7.06; N, 12.84; | A |

TABLE 2-continued

| Compound No. | Structural formula | m.p. (° C.) State | Molecular formula Elemental analysis Calcd. (%) Found (%) | Synthetic process |
| --- | --- | --- | --- | --- |
| 203 | | 153–154 Light-brown crystals | C$_{19}$H$_{23}$N$_3$O$_2$ C, 70.13; H, 7.12; N, 12.91; C, 70.18; H, 7.15; N, 12.86; | A |
| 204 | | 172–174 Colorless crystals | C$_{20}$H$_{25}$N$_3$O$_2$ C, 70.77; H, 7.42; N, 12.38; C, 70.63; H, 7.36; N, 12.38; | A |
| 205 | | 211–213 Light-brown crystals | C$_{22}$H$_{21}$N$_3$O C, 76.94; H, 6.16; N, 12.24; C, 76.83; H, 6.30; N, 12.22; | A |
| 206 | | 218–222 Light-brown crystals | C$_{16}$H$_{15}$N$_3$O.1/10H$_2$O C, 71.94; H, 5.73; N, 15.73; C, 72.02; H, 5.77; N, 15.64; | A |
| 207 | | 178–179 Light-yellow crystals | C$_{15}$H$_{14}$FN$_3$ C, 70.57; H, 5.53; N, 16.46; C, 70.65; H, 5.64; N, 16.44; | A |

TABLE 2-continued

| Compound No. | Structural formula | m.p. (° C.) State | Molecular formula Elemental analysis Calcd. (%) Found (%) | Synthetic process |
|---|---|---|---|---|
| 208 | | 165–166 Blue crystals | $C_{16}H_{16}FN_3$<br>C, 71.36; H, 5.99; N, 15.60;<br>C, 71.38; H, 6.14; N, 15.57; | A |
| 209 | | 220–221 Light-yellow crystals | $C_{15}H_{14}FN_3$<br>C, 70.57; H, 5.53; N, 16.46;<br>C, 70.54; H, 5.65; N, 16.42; | A |
| 210 | | 182–183 Blue crystals | $C_{16}H_{16}FN_3$<br>C, 71.36; H, 5.99; N, 15.60;<br>C, 71.56; H, 5.93; N, 15.65; | A |
| 211 | | 229–234 Light-brown crystals | $C_{17}H_{17}N_3O$<br>C, 73.10; H, 6.13; N, 15.04;<br>C, 72.84; H, 6.12; N, 14.83; | A |
| 212 | | 263–265 White powder | $C_{15}H_{14}N_4O$<br>C, 67.65; H, 5.30; N, 21.04;<br>C, 67.62; H, 5.29; N, 20.82; | A |
| 213 | | 171–172 Light-brown crystals | $C_{17}H_{19}N_3$<br>C, 76.95; H, 7.22; N, 15.84;<br>C, 76.87; H, 7.18; N, 15.74; | A |

TABLE 2-continued

| Compound No. | Structural formula | m.p. (° C.) State | Molecular formula Elemental analysis Calcd. (%) Found (%) | Synthetic process |
| --- | --- | --- | --- | --- |
| 214 | | 118–119 Blue plates | C₁₆H₁₉N₃ C, 75.85; H, 7.56; N, 16.59; C, 76.08; H, 7.17; N, 16.57; | A |
| 215 | | 238–239 Colorless crystals | C₂₁H₂₀N₄ C, 76.80; H, 6.14; N, 17.06; C, 77.07; H, 6.27; N, 17.08; | A |
| 216 | | 205–206 Light-yellow crystals | C₁₇H₁₈N₄O C, 69.37; H, 6.16; N, 19.03; C, 69.41; H, 6.52; N, 19.06; | A |
| 217 | | 177–178 Colorless crystals | C₂₀H₁₉N₅ C, 72.92; H, 5.81; N, 21.26; C, 73.23; H, 6.04; N, 21.21; | A |
| 218 | | 163–164 Gray powder | C₁₅H₁₆N₂O₂ C, 70.29; H, 6.29; N, 10.93; C, 70.19; H, 6.28; N, 10.95; | I |

TABLE 2-continued
| Compound No. | Structural formula | m.p. (° C.) State | Molecular formula Elemental analysis Calcd. (%) Found (%) | Synthetic process |
|---|---|---|---|---|
| 219 | 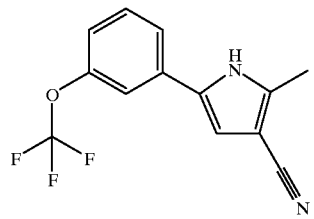 | 172–173 Colorless needles | $C_{13}H_9F_3N_2O$ C, 58.65; H, 3.41; N, 10.52; C, 58.88; H, 3.23; N, 10.63; | I |
| 220 | 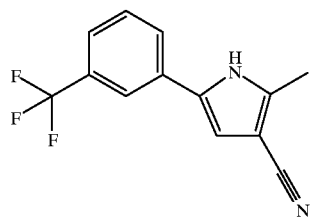 | 201–202 Colorless needles | $C_{13}H_9F_3N_2$ C, 62.40; H, 3.63; N, 11.20; C, 62.37; H, 3.74; N, 11.23; | I |
| 221 | 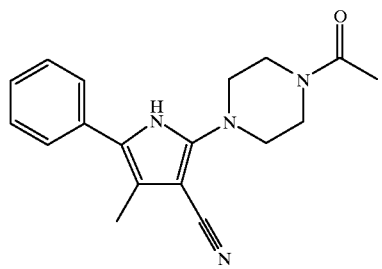 | 190–192 Light-yellow crystals | $C_{18}H_{20}N_4O$ C, 70.11; H, 6.54; N, 18.17; C, 70.88; H, 6.44; N, 18.14; | A |
| 222 | 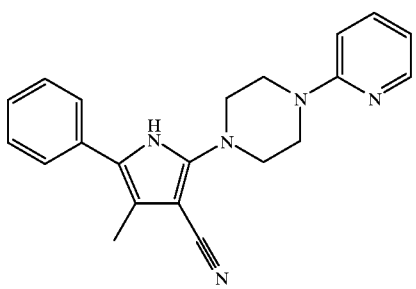 | 215–216 Light-orange crystals | $C_{21}H_{21}N_5$ C, 73.44; H, 6.16; N, 20.39; C, 73.95; H, 6.24; N, 20.34; | A |
| 223 | 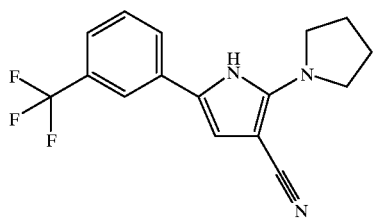 | 259–263 Colorless crystals | $C_{16}H_{14}F_3N_3$ C, 62.95; H, 4.62; N, 13.76; C, 63.01; H, 5.16; N, 13.73; | A |
| 224 | 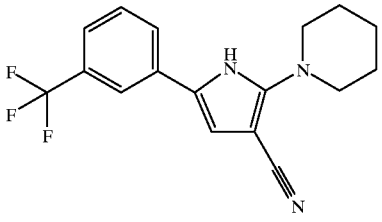 | 207–208 Light-gray crystals | $C_{17}H_{16}F_3N_3$ C, 63.94; H, 5.05; N, 13.16; C, 64.61; H, 4.83; N, 13.08; | A |

TABLE 2-continued

| Compound No. | Structural formula | m.p. (° C.) State | Molecular formula Elemental analysis Calcd. (%) Found (%) | Synthetic process |
|---|---|---|---|---|
| 225 | | 232–233 Light-brown crystals | C₁₇H₁₆F₃N₃O C, 60.89; H, 4.81; N, 12.53; C, 60.88; H, 4.92; N, 12.29; | A |
| 226 | | 252–260 Brown crystals | C₁₆H₁₈N₄O₂S C, 58.16; H, 5.49; N, 16.96; C, 57.92; H, 5.46; N, 16.84; | A |
| 227 | | 225–228 Light-yellow crystals | C₁₆H₁₄F₃N₃O C, 59.81; H, 4.39; N, 13.08; C, 60.06; H, 4.58; N, 13.08; | A |
| 228 | | 198–200 Light-brown crystals | C₁₆H₁₇N₃O C, 71.89; H, 6.41; N, 15.72; C, 72.02; H, 6.37; N, 15.77; | A |
| 229 | | 172–174 Light-yellow crystals | C₁₇H₁₉N₃O C, 72.57; H, 6.81; N, 14.94; C, 72.60; H, 6.76; N, 14.51; | A |
| 230 | | 210–216 Light-brown crystals | C₁₆H₁₈N₄O₂S C, 58.16; H, 5.49; N, 16.96; C, 58.06; H, 5.64; N, 16.82; | A |

TABLE 2-continued

| Compound No. | Structural formula | m.p. (° C.) State | Molecular formula Elemental analysis Calcd. (%) Found (%) | Synthetic process |
|---|---|---|---|---|
| 231 | 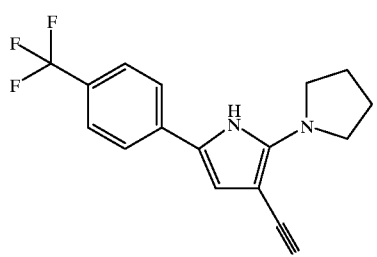 | 274–281 Light-yellow crystals | C₁₆H₁₄F₃N₃ C, 62.95; H, 4.62; N, 13.76; C, 63.19; H, 4.61; N, 13.66; | A |
| 232 | 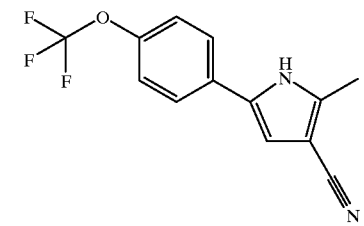 | 167–168 Colorless needles | C₁₃H₉F₃N₂O.1/10C₆H₆ C, 59.61; H, 3.53; N, 10.22; C, 59.54; H, 3.27; N, 10.43; | I |
| 233 | 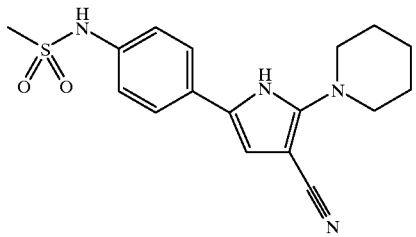 | 245–248 Gray crystals | C₁₇H₂₀N₄O₂S.C₂H₅OH C, 58.44; H, 6.71; N, 14.35; C, 58.26; H, 6.42; N, 14.58; | A |
| 234 | 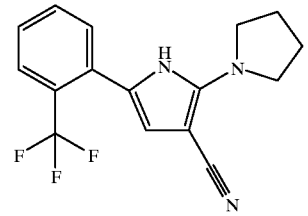 | 216–217 Colorless crystals | C₁₆H₁₄F₃N₃ C, 62.95; H, 4.62; N, 13.76; C, 63.16; H, 4.38; N, 13.76; | A |
| 235 | 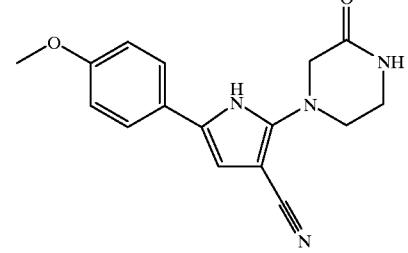 | 273–278 Light-brown powder | C₁₆H₁₆N₄O₂ C, 64.85; H, 5.44; N, 18.91; C, 64.91; H, 5.22; N, 18.99; | A |
| 236 | 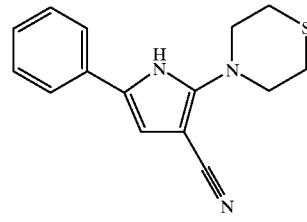 | 213–214 Light-blue crystals | C₁₅H₁₅N₃S C, 66.88; H, 5.61; N, 15.60; C, 66.81; H, 5.63; N, 15.54; | A |

TABLE 2-continued

| Compound No. | Structural formula | m.p. (° C.) State | Molecular formula Elemental analysis Calcd. (%) Found (%) | Synthetic process |
|---|---|---|---|---|
| 237 | | 252–253 Colorless crystals | $C_{16}H_{17}N_3OS$<br>C, 64.19; H, 5.72; N, 14.04;<br>C, 64.18; H, 5.76; N, 14.08; | A |
| 238 | | 155–157 Light-brown powder | $C_{18}H_{21}N_3O_2$<br>C, 69.43; H, 6.80; N, 13.49;<br>C, 69.29; H, 6.67; N, 13.46; | A |
| 239 | | 295–298 Light-brown powder | $C_{18}H_{21}N_3O$<br>C, 73.19; H, 7.17; N, 14.23;<br>C, 72.94; H, 6.92; N, 13.92; | A |
| 240 | | 163–164 Light-green crystals | $C_{19}H_{23}N_3O$<br>C, 73.86; H, 7.49; N, 13.58;<br>C, 73.80; H, 7.60; N, 13.58; | A |
| 241 | | 196–199 Yellowish green crystals | $C_{13}H_{13}N_3O$<br>C, 68.70; H, 5.77; N, 18.49;<br>C, 68.29; H, 5.55; N, 18.33; | A |
| 242 | | 158–161 Deep-green crystals | $C_{13}H_{15}N_3O \cdot 3/10H_2O$<br>C, 68.16; H, 6.37; N, 17.03;<br>C, 67.98; H, 5.97; N, 17.00; | A |

TABLE 2-continued

| Compound No. | Structural formula | m.p. (° C.) State | Molecular formula Elemental analysis Calcd. (%) Found (%) | Synthetic process |
|---|---|---|---|---|
| 243 | | 175–176 Light-brown crystals | $C_{13}H_{13}N_3$ C, 73.91; H, 6.20; N, 19.89; C, 73.81; H, 6.21; N, 19.77; | A |
| 244 | | 238–245 Colorless powder | $C_{16}H_{16}FN_3O$ C, 67.35; H, 5.65; N, 14.73; C, 67.42; H, 5.74; N, 14.53; | A |
| 245 | | 211–212 Blue crystals | $C_{17}H_{18}FN_3O$ C, 68.21; H, 6.06; N, 14.04; C, 68.20; H, 6.21; N, 13.73; | A |
| 246 | | 222–224 Light-brown crystals | $C_{16}H_{16}FN_3O$ C, 67.35; H, 5.65; N, 14.73; C, 67.54; H, 5.88; N, 14.66; | A |
| 247 | | 203–206 Light-brown crystals | $C_{17}H_{18}FN_3O$ C, 68.21; H, 6.06; N, 14.04; C, 68.38; H, 6.11; N, 13.96; | A |
| 248 | | 207–209 Light-brown crystals | $C_{18}H_{20}FN_3O$ C, 68.99; H, 6.43; N, 13.41; C, 69.01; H, 6.39; N, 13.32; | A |

TABLE 2-continued

| Compound No. | Structural formula | m.p. (° C.) State | Molecular formula Elemental analysis Calcd. (%) Found (%) | Synthetic process |
|---|---|---|---|---|
| 249 | | 169–171 Light-yellow crystals | C₁₇H₁₈FN₃O C, 68.21; H, 6.06; N, 14.04; C, 68.34; H, 6.12; N, 13.93; | A |
| 250 | | 142–144 Light-purple crystals | C₁₈H₂₀FN₃O C, 68.99; H, 6.43; N, 13.41; C, 69.23; H, 6.41; N, 13.31; | A |
| 251 | | 131–132 Light-red powder | C₁₅H₁₆N₂O C, 74.97; H, 6.71; N, 11.66; C, 75.07; H, 6.75; N, 11.55; | I |
| 252 | | 173–174 Colorless crystals | C₁₈H₂₁N₃O C, 73.19; H, 7.17; N, 14.23; C, 73.08; H, 7.41; N, 14.18; | A |
| 253 | | 133–134 Light-purple crystals | C₁₇H₁₉N₃O C, 72.57; H, 6.81; N, 14.94; C, 72.58; H, 6.88; N, 14.95; | A |
| 254 | | 167–168 Light-yellow crystals | C₁₅H₁₅N₃O C, 71.13; H, 5.97; N, 16.59; C, 71.09; H, 6.06; N, 16.66; | A |

TABLE 2-continued

| Compound No. | Structural formula | m.p. (° C.) State | Molecular formula Elemental analysis Calcd. (%) Found (%) | Synthetic process |
|---|---|---|---|---|
| 255 | 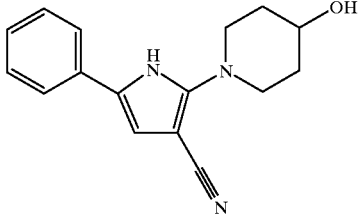 | 176–177 Blue crystals | C₁₆H₁₇N₃O C, 71.89; H, 6.41; N, 15.72; C, 71.75; H, 6.50; N, 15.76; | A |
| 256 | 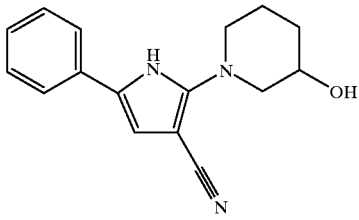 | 171–172 Purple crystals | C₁₆H₁₇N₃O C, 71.89; H, 6.41; N, 15.72; C, 71.93; H, 6.67; N, 15.71; | A |
| 257 | 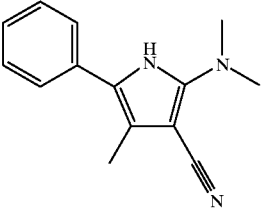 | 189–191 Bluish green crystals | C₁₄H₁₅N₃ C, 74.64; H, 6.71; N, 18.65; C, 75.09; H, 6.77; N, 18.64; | A |
| 258 | 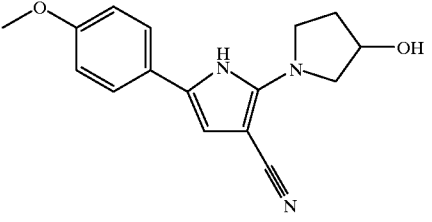 | 225–230 Colorless crystals | C₁₆H₁₇N₃O₂ C, 67.83; H, 6.05; N, 14.83; C, 68.00; H, 6,29; N, 14.83; | A |
| 259 | 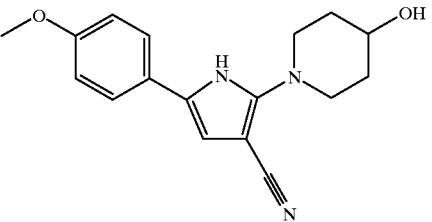 | 216–217 Colorless crystals | C₁₇H₁₉N₃O₂ C, 68.67; H, 6.44; N, 14.13; C, 68.80; H, 6.66; N, 14.14; | A |
| 260 | 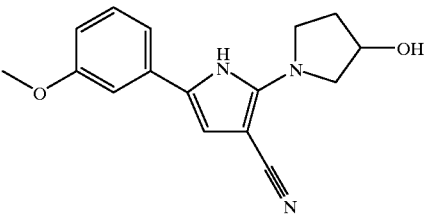 | 133–135 Colorless crystals | C₁₆H₁₇N₃O₂ C, 67.83; H, 6.05; N, 14.83; C, 67.87; H, 6.27; N, 14.81; | A |

TABLE 2-continued

| Compound No. | Structural formula | m.p. (° C.) State | Molecular formula Elemental analysis Calcd. (%) Found (%) | Synthetic process |
|---|---|---|---|---|
| 261 | | 179–181 Light-brown crystals | $C_{17}H_{19}N_3O_2$ C, 68.67; H, 6.44; N, 14.13; C, 68.43; H, 6.44; N, 13.86; | A |
| 262 | | 200–201 Light-pink crystals | $C_{16}H_{17}N_3O$ C, 71.89; H, 6.41; N, 15.72; C, 71.81; H, 6.40; N, 15.52; | A |
| 263 | | 202–204 Light-blue crystals | $C_{17}H_{19}N_3O$ C, 72.57; H, 6.81; N, 14.94; C, 72.37; H, 6.79; N, 14.57; | A |
| 264 | | 150–151 Colorless crystals | $C_{13}H_{13}N_3O$ C, 68.70; H, 5.77; N, 18.49; C, 68.63; H, 5.81; N, 18.34; | A |
| 265 | | 143–144 Colorless crystals | $C_{14}H_{15}N_3O$ C, 69.69; H, 6.27; N, 17.41; C, 69.57; H, 6.26; N, 17.33; | A |
| 266 | | 213–214 Colorless powder | $C_{13}H_9N_3$ C, 75.35; H, 4.38; N, 20.28; C, 75.34; H, 4.47; N, 20.08; | H |

TEST EXAMPLES

The following are the results of pharmacological tests of some representative species, which demonstrate the usefulness of the compound of the invention.

Test Example 1

Cystometrography (Rats)

Cystometrography is a method for ascertaining the relation between intravesical pressure and bladder capacity and provides information on the time course of condition of the urinary bladder from urine filling to micturition, the possible involuntary contraction of the urinary bladder, and the contractility of the detrusor muscle during micturition.

The experiment was performed using 9 to 13-weeks old female SD rats in groups of 3–5. After a median incision was made in the abdominal region under urethane anesthesia, a polyethylene indwelling cannula was inserted into the urinary bladder dome through the apex of the urinary bladder and fixed. The other end of the cannula was connected to a T-tube for infusion of saline via one branch and changes in intravesical pressure were recorded via the other branch. When warmed saline was continuously infused into the urinary bladder at a constant rate, the urinary bladder was distended and, when the pressure reached a threshold, the urinary bladder underwent rapid contractions and at the same time a micturition was induced. This procedure was repeated until the volume of saline from the start of infusion to the threshold intravesical pressure (bladder capacity) became steady giving approximately constant values in at least two consecutive determinations. Then, the test compound was administered into the duodenum. The bladder capacity was measured immediately before administration of the test compound and 0.5, 1, 2, and 3 hours after administration. The maximum increase rate (%) in bladder capacity was calculated by means of the following equation.

$$\text{Maximum increase rate in bladder capacity} = [(A-B)/B] \times 100$$

where B represents the bladder capacity value immediately before administration of the test compound and A represents the maximum bladder capacity at 0.5, 1, 2, and 3 hours after administration of the test compound. Results of the test are shown in Table 3. The data shown are mean values.

TABLE 3

Cystometrography (rats)

| Compound No. | Dosage (mg/kg) | Maximum increase rate (%) in bladder capacity |
|---|---|---|
| R1 | 3 | 63.6 |
| 1 | 3 | 60.8 |
| 8 | 30 | 55.4 |
| 15 | 10 | 53.8 |
| 41 | 10 | 38.8 |
| 63 | 3 | 49.9 |
| Propiverine | 100 | 42.0 |

(Compound No. corresponds to that in Table 1 or 2)

The compounds of the invention produced equivalent or more potent effect in the increase of bladder capacity at markedly lower dose levels as compared with the reference prior art drug.

It is clear from the above results that the compounds of the invention have potent bladder capacity increasing activity.

Test Example 2

Acute Toxicity Test

Male ddY mice, 6 to 7-weeks old, were used in groups of 4–5. The animals fasted from the previous days (16–18 hours before the experiment) were given the test compound by oral gavage using a gastric tube and monitored for death for 2 weeks. As shown in Table 4, no death was encountered at all, nor was observed any abnormal finding.

TABLE 4

Acute toxicity test in mice

| Compound No. | Dosage (mg/kg) | Dead/Total |
|---|---|---|
| R1 | 1000 | 0/4 |
| 1 | 1000 | 0/4 |
| 8 | 1000 | 0/4 |
| 41 | 1000 | 0/5 |
| 63 | 1000 | 0/5 |

Formulation Example 1

| Tablets (oral dosage form) In 200 mg per tablet: | |
|---|---|
| Compound No. R1 | 20 mg |
| Corn starch | 88 mg |
| Crystalline cellulose | 80 mg |
| Carboxymethylcellulose calcium | 10 mg |
| Light silicic anhydride | 1 mg |
| Magnesium stearate | 1 mg |

A powdery mixture of the above composition was compressed to provide oral tablets.

Formulation Example 2

| Tablets (oral dosage form) In 200 mg per tablet | |
|---|---|
| Compound No. 1 | 20 mg |
| Corn starch | 88 mg |
| Crystalline cellulose | 80 mg |
| Carboxymethylcellulose calcium | 10 mg |
| Light silicic anhydride | 1 mg |
| Magnesium stearate | 1 mg |

A powdery mixture of above composition was compressed to provide oral tablets.

Formulation Example 3

| Tablets (oral dosage form) In 200 mg per tablet: | |
|---|---|
| Compound No. 63 | 20 mg |
| Corn starch | 88 mg |
| Crystalline cellulose | 80 mg |
| Carboxymethylcellulose calcium | 10 mg |
| Light silicic anhydride | 1 mg |
| Magnesium stearate | 1 mg |

A powdery mixture of the above composition was compressed to provide oral tablets.

INDUSTRIAL APPLICABILITY

As described above, the compound of the present invention has potent bladder capacity increasing activity with a low toxic potential and is, therefore, useful for the treatment of pollakiuria or urinary incontinence.

What is claimed is:

1. A pharmaceutical composition for treating pollakiuria or urinary incontinence which comprises a therapeutically effective amount of a compound of the formula [1],

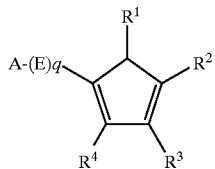

[1]

a pharmaceutically acceptable salt thereof or a solvate of them in combination with a pharmaceutically acceptable inert diluent or carrier;

wherein $R^1$ is hydrogen or alkoxycarbonylamino;
$R^2$ is

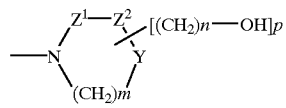

$Z^1$ and $Z^2$ are the same or different and each is —$CH_2$— or >C=O; provided that $Z^1$ and $Z^2$ do not concurrently represent >C=O;

Y is —$CH_2$—;

m is 1; n is an integer of 0–2; p is 0 or 1;

$R^3$ is cyano or carbomoyl;

$R^4$ is hydrogen or alkyl;

E is alkylene; q is 0 or 1;

A is (1) methyl, or (2) aryl which is optionally substituted;

when A is aryl which is optionally substituted, the aryl is optionally substituted by 1 group or 2–3 different groups selected from the group consisting of (1) halogen, (2) alkyl which is optionally substituted by halogen, (3) cyano, (4) nitro, (5) alkoxycarbonyl, (6) hydroxy, (7) alkoxy which is optionally substituted by halogen, or aryl which is optionally substituted by alkoxy, or alkoxy, (8) —$NHSO_2R^{92}$, and (9) —$NR^{93}R^{94}$;

$R^{92}$ is (1) alkyl or (2) aryl which is optionally substituted by alkyl;

$R^{93}$ and $R^{94}$ are the same or different and each is (1) hydrogen, (2) alkyl, or (3) acyl; or $R^{93}$ and $R^{94}$ jointly and taken together with the adjacent N atom represent 1-pyrrolidinyl.

2. The pharmaceutical composition according to claim 1, wherein $R^2$ is 1-pyrrolidinyl.

3. The pharmaceutical composition according to claim 1, wherein $R^1$ is hydrogen, $R^2$ is 1-pyrrolidinyl, $R^3$ is cyano, $R^4$ is hydrogen or alkyl, q is equal to 0, and A is aryl which is optionally substituted.

4. The pharmaceutical composition according to claim 1, wherein the active ingredient is 3-cyano-5-(3-ethoxyphenyl)-2-(1-pyrrolidinyl)pyrrole.

5. A compound of the formula [1],

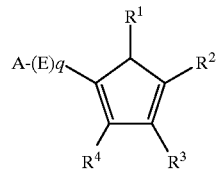

[1]

a pharmaceutically acceptable salt thereof or a solvate of them;

wherein $R^1$ is hydrogen or alkoxycarbonylamino;
$R^2$ is

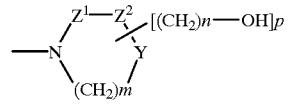

$Z^1$ and $Z^2$ are the same or different and each is —$CH_2$— or >C=O; provided that $Z^1$ and $Z^2$ do not concurrently represent >C=O;

Y is —$CH_2$—;

m is 1; n is an integer of 0–2; p is 0 or 1;

$R^3$ is cyano or carbamoyl;

$R^4$ is hydrogen or alkyl;

E is alkylene; q is 0 or 1;

A is (1) methyl, or (2) aryl which is optionally substituted;

when A is aryl which is optionally substituted, the aryl is optionally substituted by 1 group of 2–3 different groups selected from the group consisting of (1) halogen, (2) alkyl which is optionally substituted by halogen, (3) cyano, (4) nitro, (5) alkoxycarbonyl, (6) hydroxy, (7) alkoxy which is optionally substituted by halogen, or aryl which is optionally substituted by alkoxy, or alkoxy, (8) —$NHSO_2R^{92}$, and (9) —$NR^{93}R^{94}$;

$R^{92}$ is (1) alkyl or (2) aryl which is optionally substituted by alkyl;

$R^{93}$ and $R^{94}$ are the same or different and each is (1) hdyrogen, (2) alkyl, or (3) acyl; or $R^{93}$ and $R^{94}$ jointly and taken together with the adjacent N atom represent 1-pyrrolidinyl but exclusive of the following cases:

(1) $R^1$ is hydrogen, $R^2$ is 1-pyrrolidinyl, $R^3$ is cyano, $R^4$ is hydrogen, q is equal to 0, and A is phenyl, 4-bromophenyl, 4-nitrophenyl, or 2,4-dimethylphenyl, (2) $R^1$ is hydrogen, $R^2$ is 2-oxopyrrolidin-1-yl, $R^3$ is cyano, $R^4$ is methyl, q is equal to 0, and A is methyl.

6. The compound according to claim 5, a salt thereof or a solvate thereof, wherein $R^2$ is 1-pyrrolidinyl.

7. The compound according to claim 5, a salt thereof or a solvate thereof, wherein $R^1$ is hydrogen, $R^2$ is 1-pyrrolidinyl, $R^3$ is cyano, $R^4$ is hydrogen or alkyl, q is equal to 0, and A is aryl which is optionally substituted.

8. The compound according to claim 5, a salt thereof or a solvate thereof, which is 3-cyano-5-(3-ethoxyphenyl)-2-(1-pyrrolidinyl)pyrrole.

* * * * *

UNITED STATES PATENT AND TRADEMARK OFFICE
CERTIFICATE OF CORRECTION

PATENT NO. : 6,172,102 B1
DATED : January 9, 2001
INVENTOR(S) : Tsuda, M., Tanaka, S. and Nakamura, A.

It is certified that error appears in the above-identified patent and that said Letters Patent is hereby corrected as shown below:

<u>Title page,</u>
Item [57], ABSTRACT,
The formula 1 should be corrected to read:

--
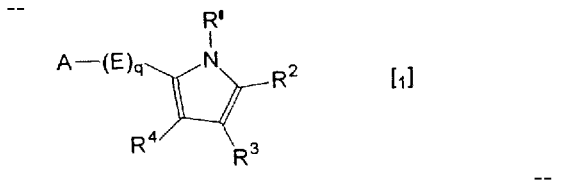
[1]
--

<u>Columns 17, 129 and 130,</u>
The formula 1 should be corrected to read:

--
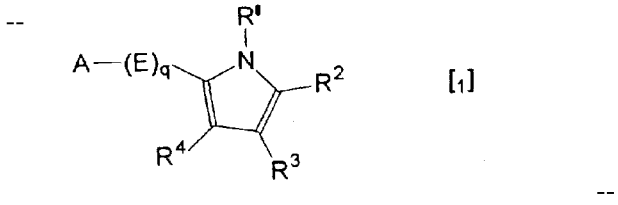
[1]
--

Signed and Sealed this

Eighth Day of October, 2002

*Attest:*

*Attesting Officer*

JAMES E. ROGAN
*Director of the United States Patent and Trademark Office*